United States Patent
Wilson et al.

(10) Patent No.: US 11,154,569 B2
(45) Date of Patent: Oct. 26, 2021

(54) RUTHENIUM μ-NITRIDO COMPLEXES AND THEIR USE AS CALCIUM UPTAKE INHIBITORS

(71) Applicants: CORNELL UNIVERSITY, Ithaca, NY (US); TEMPLE UNIVERSITY, Philadelphia, PA (US)

(72) Inventors: Justin Wilson, Ithaca, NY (US); Madesh Muniswamy, Philadelphia, PA (US); Sarah R. Nathan, Ithaca, NY (US)

(73) Assignees: CORNELL UNIVERSITY, Ithaca, NY (US); TEMPLE UNIVERSITY, Philadelphia, PA (US)

( * ) Notice: Subject to any disclaimer, the term of this patent is extended or adjusted under 35 U.S.C. 154(b) by 0 days.

(21) Appl. No.: 16/277,246

(22) Filed: Feb. 15, 2019

(65) Prior Publication Data
US 2019/0247427 A1 Aug. 15, 2019

Related U.S. Application Data

(60) Provisional application No. 62/631,103, filed on Feb. 15, 2018.

(51) Int. Cl.
*A61K 33/24* (2019.01)
*A61P 43/00* (2006.01)
*C01G 55/00* (2006.01)

(52) U.S. Cl.
CPC .............. *A61K 33/24* (2013.01); *A61P 43/00* (2018.01); *C01G 55/008* (2013.01)

(58) Field of Classification Search
CPC ................................................. A61K 33/24
See application file for complete search history.

(56) References Cited

PUBLICATIONS

Urgiles, J., et al., Dinuclear nitrido-bridged ruthenium complexes bearing diimine ligands, Dalton Trans., Oct. 10, 2017, 46, 14256.*
Alessio E. "Thirty Years of the Drug Candidate NAMI-A and the Myths in the Field of Ruthenium Anticancer Compounds: A Personal Perspective", Eur. J. Inorg. Chem., (2017), pp. 1549-1560 DOI: 10.1002/ejic.201600986.
Cleare M.J. et al., "Polynuclear Nitrido-complexes of Osmium, Ruthenium, and Iridium", J. Chem. Soc. (A), (1970), pp. 1117-1125.
Emerson J. et al., "The Component of 'Ruthenium Red' Responsible for Inhibition of Mitochondrial Calcium Ion Transport. Spectra, Electrochemistry, and Aquation Kinetics. Crystal Structure of u—O—[(HCO2)(NH3)4Ru]2Cl3", J. Am. Chem. Soc., (1993), 115, pp. 11799-11805.
Lee S.K. et al., "Structural Insights into Mitochondrial Calcium Uniporter Regulation by Divalent Cations", Cell Chemical Biology, (2016), 23, pp. 1157-1169 http://dx.doi.org/10.1016/j.chembiol.2016.07.012.
Matlib M.A. et al., "Oxygen-bridged Dinuclear Ruthenium Amine Complex Specifically Inhibits Ca2+ Uptake into Mitochondria in Vitro and in Situ in Single Cardiac Myocytes", The Journal of Biological Chemistry, (1998), 273(17), pp. 10223-10231 doi: 10.1074/jbc.273.17.10223.
Nathan S.R. et al., "Synthesis and Evaluation of a Ruthenium-based Mitochondrial Calcium Uptake Inhibitor", Journal of Visualized Experiments, (2017), 128, 6 pages doi: 10.3791/56527.
Nathan S.R. et al., "Synthetic Methods for the Preparation of a Functional Analogue of Ru360, a Potent Inhibitor of Mitochondrial Calcium Uptake", Inorganic Chemistry, (2017), 56, pp. 3123-3126 DOI: 10.1021/acs.inorgchem.6b03108.
Nathan S.R. et al., Synthesis and characterization of dinuclear ruthenium complexes as mitochondrial calcium uptake inhibitors, 254th National Meeting and Exposition of the American-Chemical-Society (ACS) on Chemistry's Impact on the Global Economy, (2017), Washington, DC.
Urgiles J. et al., "Dinuclear nitrido-bridged ruthenium complexes bearing diimine ligands", Dalton Transactions, (2017), 46, pp. 14256-14263 DOI: 10.1039/c7dt03085a.
Woods J.J. et al., "A Selective and Cell-Permeable Mitochondrial Calcium Uniporter (MCU) Inhibitor Preserves Mitochondrial Bioenergetics after Hypoxia/Reoxygenation Injury", ACS Central Science, (2019), 5, pp. 153-166 DOI: 10.1021/acscentsci.8b00773.
Ying W-L. et al., "Inhibition of Mitochondrial Calcium Ion Transport by an Oxo-Bridged Dinuclear Ruthenium Ammine Complex", Biochemistry, (1991), 30, pp. 4949-4952.

* cited by examiner

*Primary Examiner* — H. Sarah Park
(74) *Attorney, Agent, or Firm* — Scully, Scott, Murphy & Presser, P.C.

(57) ABSTRACT

A method for treating or preventing a disease or condition that operates by calcium transport through the mitochondrial calcium uniporter (MCU), the method comprising administering to a subject a therapeutically effective amount of an MCU inhibitor having the following structure:

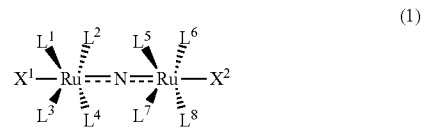

(1)

wherein $L^1$, $L^2$, $L^3$, $L^4$, $L^5$, $L^6$, $L^7$, $L^8$, $X^1$, and $X^2$ are independently selected from halide, amine groups —$NR^1R^2R^3$, phosphine groups —$PR^5R^6R^7$, carboxylate groups $R^4C(O)O$—, and solvent molecules, and provided that at least one of $L^1$, $L^2$, $L^3$, $L^4$, $L^5$, $L^6$, $L^7$, $L^8$, $X^1$, and $X^2$ is selected from amine or phosphine groups; wherein $R^1$, $R^2$, $R^3$, and $R^4$ are independently selected from hydrogen atoms and hydrocarbon groups having up to six carbon atoms, wherein two of $R^1$, $R^2$, and $R^3$ within a —$NR^1R^2R^3$ group are optionally interconnected to form an N-containing ring; and R groups in adjacent amino or phosphine groups may optionally interconnect.

13 Claims, 9 Drawing Sheets
(8 of 9 Drawing Sheet(s) Filed in Color)

4A

4B

4C

RUTHENIUM µ-NITRIDO COMPLEXES AND THEIR USE AS CALCIUM UPTAKE INHIBITORS

CROSS REFERENCE TO RELATED APPLICATION

This application claims the benefit of priority from U.S. Provisional Application No. 62/631,103, filed on Feb. 15, 2018.

FIELD OF THE INVENTION

The invention generally relates to ruthenium complexes and their use in methods for treating conditions involving cellular calcium uptake. The invention is more particularly directed to ruthenium complexes coordinated to amine or phosphine ligands and their use as inhibitors of the mitochondrial calcium uniporter, to treat such conditions as reperfusion injury, such as of the heart or brain.

BACKGROUND OF THE INVENTION

Intracellular calcium ($Ca^{2+}$) ion concentration plays a crucial role in signal transduction and bioenergetics. Plasma membrane depolarization or the stimulation of receptors, such as the inositol triphosphate receptors ($InsP_3Rs$) or ryanodine receptors (RYRs), produces a transient intracellular $Ca^{2+}$ increase. This $Ca^{2+}$ increase is achieved by both influx from the extracellular milieu in addition to $Ca^{2+}$ release from the endoplasmic reticulum (ER) and sarcoplasmic reticulum (SR) (e.g., M. Berridge et al., Nat. Rev. Mol. Cell Biol. 2003, 4, 517-529). Under these conditions, the highly selective and inward rectifying $Ca^{2+}$ channel, known as the mitochondrial calcium uniporter (MCU), acts to clear excessive cytosolic $Ca^{2+}$ (e.g., Y. Kirichok et al., Nature, 2004, 427, 360-364). In this capacity, mitochondria act as $Ca^{2+}$ sinks, shaping cytosolic $Ca^{2+}$ ($_cCa^{2+}$) transients, while also utilizing these ions for cellular energy production.

The MCU complex comprises multiple functional domains with the MCU as the central pore-forming subunit (e.g., J. M. Baughman et al., Nature, 2011, 476, 341-345). The MCU subunit is a 351-amino acid residue long motif with the N- and C-terminal domains both located in the inner mitochondrial matrix (IMM) (e.g., K. Oxenoid et al., Nature, 2016, 533, 269-273). The transmembrane domains (TM1 and TM2) are connected through the solvent accessible region with a highly conserved DXXE motif located in the upper helix of TM2 (e.g., A. G. Bick et al., Science, 2012, 336, 886). The MCU pore is constructed from four of these subunits, giving a tetrameric structure (e.g., R. Baradaran et al., Nafture, 2018, 559, 580-584). MCU-mediated mitochondrial $Ca^{2+}$ uptake is regulated by the proteins MCUR1, EMRE, MICU1, and MICU2. A 2-3 µM rise in $_cCa^{2+}$ concentration causes MICU1 and MICU2 to dissociate from the MCU, thus opening the pore for $Ca^{2+}$ uptake (e.g., C. Petrungaro et al., Cell Metab. 2015, 22, 721-733). MCUR1, in contrast, acts as a positive regulator for $_cCa^{2+}$ uptake by binding to the coiled-coil region of the N-terminal domain (NTD, residues 72-189) within the IMM (e.g., Y. Lee et al., EMBO Rep. 2015, 16, 1318-1333). Like most $Ca^{2+}$ channels, the MCJ is additionally auto-regulated by divalent cations such as $Mg^{2+}$ and $Ca^{2+}$. Binding of divalent cations to the MCU-regulating acidic patch (MRAP) region in the β-grasp-like fold of the NTD destabilizes and shifts the self-association equilibrium of the MCU pore domain towards monomer formation. This equilibrium shift inhibits MCU function, thus fine-tuning $Ca^{2+}$ entry into the mitochondria.

MCU-mediated $Ca^{2+}$ uptake into the mitochondria is an electrogenic process that is driven by the highly negative electrochemical gradient across the IMM (e.g., T. E. Gunter et al., Am J. Physiol., 1994, 267, C313-319). The surge of MCU-mediated mitochondrial $Ca^{2+}$ ($_mCa^{2+}$) uptake allosterically stimulates the mitochondrial matrix pyruvate dehydrogenase complex, α-keto-glutarate dehydrogenase, and isocitrate enzymes to generate reducing equivalents (NADH) and promote ATP production (e.g., G. Hajnoczky et al., Cell 1995, 82, 415-424). Although MCU-mediated mitochondrial $Ca^{2+}$ uptake is essential for bioenergetics, $Ca^{2+}$ overload via this pathway triggers opening of the mitochondrial permeability transition pore (mPTP), which gives rise to mitochondrial swelling and rupture, creating a cellular bioenergetic crisis and activating degradative enzymes under pathological conditions, which leads to irreversible cell damage and death (e.g., P. Bernardi, Physiol. Rev. 1999, 79, 1127-1155). Dysregulation of $Ca^{2+}$ uptake by the MCU plays a major role in numerous pathological conditions, such as ischemic reperfusion injury (e.g., S. Marchi et al., J. Physiol. 2014, 592, 829-839) and neurodegenerative disease (e.g., Y. V. Medvedeva et al., Neurobiol. Dis. 2014, 68, 137-144). As such, pharmacological strategies to regulate MCU activity are of great importance and may provide further insight into the role of this channel in mediating human disease.

With the significant recent interest within this field, systematic efforts to find selective and cell-permeable MCU inhibitors have only recently been initiated. However, the structural criteria required for small molecules to be effective inhibitors of the MCU is not well established. As such, combinatorial screening strategies have recently been employed to discover organic molecules that possess MCU-inhibitory properties (e.g., D. M. Arduino et al., Mol. Cell 2017, 67, 711-723.e7). Despite the discovery of several organic small-molecule MCU inhibitors, these compounds generally have alternative biological activities, which result in undesirable toxicity (e.g., Arduino et al., supra, and N. Kon et al., Cell Death Discov. 2017, 3, 17045). For example, mitoxantrone was recently discovered via a combinatorial approach to be a cell-permeable MCU inhibitor (e.g., Arduino et al., supra). This compound, however, is an established topoisomerase II inhibitor that has been employed as a cytotoxic agent for the treatment of cancer (e.g., J. Kapuscinski et al., Biochem. Pharmacol. 1985, 34, 4203-4213). In addition to these secondary biological applications, it also gives rise to cardiotoxicity, which could hamper its in vivo applications (e.g., H Nagele et al., J. Hear. Lung Transplant. 2004, 23, 641-643; and M. Goebel et al., Oncol. Res. Treat. 1992, 15, 198-204).

A well known MCU inhibitor is the inorganic binuclear oxo-bridged ruthenium complex ruthenium 360 (i.e., Ru360, shown in FIG. 1A), which was named for its strong absorbance at 360 nm. Although Ru360 is a highly potent and selective MCU inhibitor (e.g., W.-L. Ying et al., Biochemistry 1991, 30, 4949-4952), its widespread applicability in biological systems is limited by several factors. For example, in most cell lines, this compound is impermeant to the plasma membrane, hindering its use in intact cellular models. Furthermore, the synthesis of this complex is challenging and low-yielding (e.g., S. R. Nathan et al., Inorg. Chem. 2017, 56, 3123-3126), which diminishes its widespread availability. Thus, there is a need in the art for alternative MCU-inhibiting compounds that have greater potency and/or cell permeability, along with low toxicity, and which can be synthesized by a more straight-forward process in better yields.

SUMMARY OF THE INVENTION

In one aspect, the present disclosure is directed to ruthenium complexes that function as highly potent cell-permeable MCU inhibitors with low toxicity. The MCU inhibitors described herein can also advantageously be prepared by straight-forward synthetic methods. A salient feature of the ruthenium complexes is the presence of a t-nitrido bridging atom between two ruthenium atoms, and at least one, two, three, four, or more amine and/or phosphine groups on one or both of the ruthenium atoms. In more specific embodiments, the ruthenium complexes have the following structure:

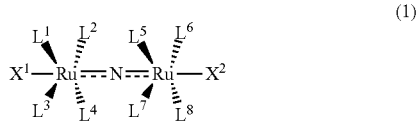

(1)

In Formula (1), $L^1$, $L^2$, $L^3$, $L^4$, $L^5$, $L^6$, $L^7$, $L^8$, $X^1$, and $X^2$ are independently selected from halide, amine groups (—$NR^1R^2R^3$), phosphine groups (—$PR^5R^6R^7$), carboxylate groups ($R^4C(O)O$—), and solvent molecules, wherein each Ru atom is bound to no more than two solvent molecules, and provided that at least one of $L^1$, $L^2$, $L^3$, $L^4$, $L^5$, $L^6$, $L^7$, $L^8$, $X^1$, and $X^2$ are selected from amine or phosphine groups; $R^1$, $R^2$, $R^3$, and $R^4$ are independently selected from hydrogen atoms and hydrocarbon groups having up to six carbon atoms, wherein two of $R^1$, $R^2$, and $R^3$ within a —$NR^1R^2R^3$ group are optionally interconnected to form an N-containing ring; and, in the event of two adjacent groups on a Ru atom being —$NR^1R^2R^3$ groups, the adjacent $R^1$ groups or adjacent $R^2$ groups or adjacent $R^3$ groups may be interconnected to form a bidentate ligand on the Ru atom; $R^5$, $R^6$, and $R^7$ are independently selected from hydrocarbon groups having up to six carbon atoms, wherein two of $R^5$, $R^6$, and $R^7$ within a —$PR^5R^6R^7$ group are optionally interconnected to form a P-containing ring; and, in the event of two adjacent groups on a Ru atom being —$PR^5R^6R^7$ groups, the adjacent $R^5$ groups or adjacent $R^6$ groups or adjacent $R^7$ groups may be interconnected to form a bidentate ligand on the Ru atom; and depending on the oxidation state of the Ru atoms and selection of groups bound to the Ru atoms, the inhibitor compound shown in Formula (1) may have an overall positive or negative charge, which necessitates an association with one or more anions or cations to establish overall charge neutrality of the compound in Formula (1). Typically, each Ru atom is considered to have a +4 charge and the bridging nitride is considered to have a −3 charge.

In another aspect, the present disclosure is directed to a method for treating or preventing a disease or condition that operates by calcium transport through the mitochondrial calcium uniporter (MCU). The method includes administering to a subject having such a disease or condition a therapeutically (pharmaceutically) effective amount of a ruthenium complex according to Formula (1), as described above, to effectively inhibit the MCU. In specific embodiments, the disease or condition is reperfusion injury, particularly of cardiac or brain tissue, or reperfusion injury associated with organ transplantation. In some embodiments, the method prevents reperfusion injury in bodily tissue by administering the inhibiting compound after an ischemic event and before reperfusion of oxygen to bodily tissue. In other embodiments, the method treats reperfusion injury by resulting in at least partial restoration of bodily tissue that has been damaged by an ischemic event followed by reperfusion injury. The method can also treat or prevent hypoxia/reoxygenation injury, sepsis-induced MCU oxidation, or mitochondrial dysfunction. In particular embodiments, the compounds described herein are used to protect cardiomyocytes from the $mCa^{2+}$ overload that occurs during hypoxia/reoxygenation (H/R) injury and prevent mPTP opening and mitochondrial swelling. In other particular embodiments, the compounds described herein are used to effect substantial or complete suppression of sepsis-induced MCU oxidation.

BRIEF DESCRIPTION OF THE FIGURES

The patent or application contains at least one drawing executed in color. Copies of this patent or patent application publication with color drawing(s) will be provided by the Patent and Trademark Office upon request and payment of the necessary fee.

In FIG. 4D, a representative trace depicts the comparison of C-2 and Ru360.

DETAILED DESCRIPTION OF THE INVENTION

Figures 1A, 1B:
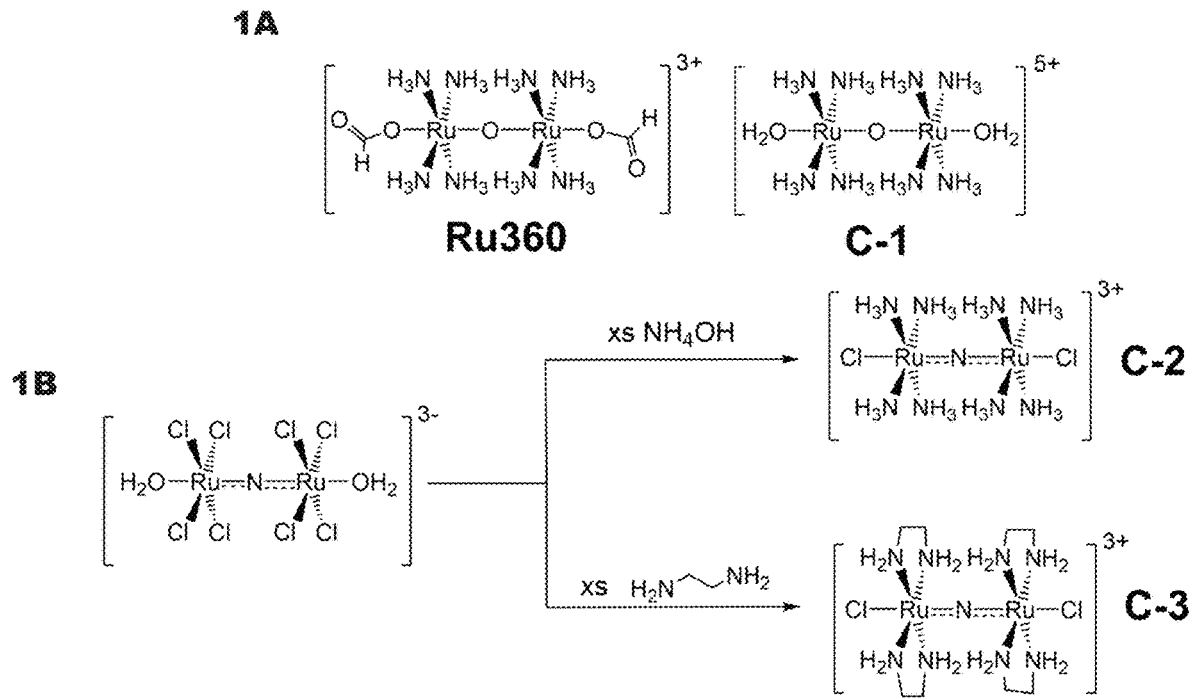
FIG. 1A shows the chemical structures of Ru360 and $[Ru_2(\mu\text{-}O)(NH_3)_8(H_2O)_2]^{+5}$ (C-1), both of the art.
FIG. 1B shows a simplified and generalized synthetic scheme for the preparation of two compounds of the invention: $[Ru_2(\mu\text{-}N)(NH_3)_8Cl_2]^{+3}$ (C-2) and $[Ru_2(\mu\text{-}N)(en)_4Cl_2]^{+3}$ (C-3), where en=ethylenediamine.

The term "hydrocarbon group," as also denoted below by various "R" groups, generally refers to groups containing at least one and up to six carbon atoms. In different embodiments, the hydrocarbon group independently contains one, two, three, four, five, or six carbon atoms, or a number of carbon atoms within a range bounded by any of the above carbon numbers. In the case where R is a cyclic hydrocarbon having three, four, five, or six ring carbon atoms, the cyclic hydrocarbon may or may not be substituted with one, two, three, or four methyl groups. Thus, the potential exists for a cyclic hydrocarbon group to possess up to ten carbon atoms. The hydrocarbon group can be saturated or unsaturated, straight-chained or branched, and cyclic or acyclic.

In a first set of embodiments, one or more of the hydrocarbon groups (R) are saturated. For example, in some embodiments, one or more of the hydrocarbon groups are saturated and straight-chained, i.e., straight-chained alkyl groups. Some examples of straight-chained alkyl groups include methyl, ethyl, n-propyl, n-butyl, n-pentyl, and n-hexyl groups. In other embodiments, one or more of the hydrocarbon groups are saturated and branched, i.e., branched alkyl groups. Some examples of branched alkyl groups include isopropyl (2-propyl), isobutyl (2-methylprop-1-yl), sec-butyl (2-butyl), i-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, wherein the "1-yl" suffix represents the point of attachment of the group. In other embodiments, one or more of the hydrocarbon groups are saturated and cyclic, i.e., cycloalkyl groups. Some examples of cycloalkyl groups include cyclopropyl, 1-methylenecyclopropyl (i.e., with presence of a methylene linker), 2-methylcycloprop-1-yl, 2,3-dimethylcycloprop-1-yl, cyclobutyl, 1-methylenecyclobutyl, 2-methylcyclobut-1-yl, 2,4-dimethylcyclobut-1yl, cyclopentyl, 1-methylenecyclopentyl, 2-methylcyclopent-1-yl, 2,5-dimethylcyclopent-1-yl, 3,4-dimethylcyclopent-1-yl, cyclohexyl, 1-methylenecyclohexyl, 2-methylcyclohex-1-yl, 2,6-dimethylcyclohex-1-yl, and 3,5-dimethylcyclohex-1-yl groups.

In a second set of embodiments, one or more of the hydrocarbon groups (R) are unsaturated. For example, in some embodiments, one or more of the hydrocarbon groups are unsaturated and straight-chained. The unsaturation occurs by the presence of one or more carbon-carbon double bonds (i.e., straight-chained olefinic or alkenyl groups) and/or one or more carbon-carbon triple bonds (i.e., straight-chained alkynyl groups). Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, and 1,3,5-hexatrien-1-yl. Some examples of straight-chained alkynyl groups include ethynyl and propargyl (2-propynyl) groups. In other embodiments, one or more of the hydrocarbon groups are unsaturated and branched, i.e., branched alkenyl or alkynyl groups. Some examples of branched alkenyl groups include propen-2-yl ($CH_2$=C—$CH_3$), 1-buten-2-yl ($CH_2$=C.—$CH_2$—$CH_3$), 1-buten-3-yl ($CH_2$=CH—CH.—$CH_3$), 1-propen-2-methyl-3-yl ($CH_2$=CC($CH_3$)—$CH_2$—), 1-penten-4-yl, 1-penten-3-yl, 1-penten-2-yl, 2-penten-2-yl, 2-penten-3-yl, 2-penten-4-yl, and 1,4-pentadien-3-yl, wherein the dot in any of the foregoing groups indicates a point of attachment. In other embodiments, one or more of the hydrocarbon groups are unsaturated and cyclic, i.e., cycloalkenyl groups. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, 2-methylphenyl (o-tolyl), 3-methylphenyl (m-tolyl), 4-methylphenyl (μ-tolyl), 2,6-dimethylphenyl, 3,5-dimethylphenyl, 3,4,5-trimethylphenyl, 2,3,5,6-tetramethylphenyl, 2-methylbenzyl, 3-methylbenzyl, 4-methylbenzyl, 2,6-dimethylbenzyl, 3,5-dimethylbenzyl, and 3,4,5-trim ethylbenzyl groups.

In a first aspect, the present disclosure is directed to ruthenium complexes and compositions containing these complexes. The ruthenium atoms can have any suitable oxidation state; however, the ruthenium atoms are typically in the +4 oxidation state. Each of the two ruthenium atoms are generally hexa-coordinate, including the μ-nitrido bridge. More specifically, the ruthenium complexes have the following structure:

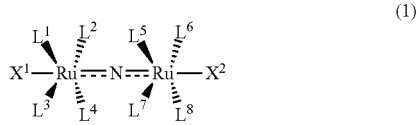

(1)

In Formula (1) above, $L^1$, $L^2$, $L^3$, $L^4$, $L^5$, $L^6$, $L^7$, $L^8$, $X^1$, and $X^2$ are independently selected from halide (e.g., fluoride, chloride, bromide, or iodide), amine groups (i.e., —$NR^1R^2R^3$), phosphine groups (i.e., —$PR^5R^6R^7$), carboxylate groups (i.e., $R^4C(O)O$—), and solvent molecules, wherein each Ru atom is bound to no more than two solvent molecules.

In accordance with convention, the solid wedged lines indicate forward facing bonds while the dashed wedged lines indicate backward (receding) facing bonds. The dashed lines at the central (μ-nitrido) nitrogen atom indicate the presence of double bond character. For purposes of the invention, a provision is included that at least one of $L^1$, $L^2$, $L^3$, $L^4$, $L^5$, $L^6$, $L^7$, $L^8$, $X^1$, and $X^2$ is selected from amine or phosphine groups. In a first set of embodiments, at least one, i.e., one, two, three, four, five, six, seven, or eight (i.e., all) of $L^1$, $L^2$, $L^3$, $L^4$, $L^5$, $L^6$, $L^7$, and $L^8$ (also referred to as "L groups") are selected from amine groups, while $X^1$ and $X^2$ (also referred to as "X groups") may or may not also be amine groups. If $X^1$ and $X^2$ are not amine groups, they may be selected from halide atoms, phosphine groups, carboxylate groups, or solvent molecules. In a second set of embodiments, at least one, i.e., one, two, three, four, five, six, seven, or eight (i.e., all) of $L^1$, $L^2$, $L^3$, $L^4$, $L^5$, $L^6$, $L^7$, and $L^8$ are selected from phosphine groups, while $X^1$ and $X^2$ may or may not also be phosphine groups. If $X^1$ and $X^2$ are not phosphine groups, they may be selected from halide atoms, amine groups, carboxylate groups, or solvent molecules. In all embodiments, $X^1$ and $X^2$ may also be the same or different.

In a first particular set of embodiments, $L^1$ is an amine or phosphine group; $L^2$, $L^3$, $L^4$, $L^5$, $L^6$, $L^7$, and $L^8$ are halide atoms; and $X^1$ and $X^2$ are independently selected from halide, carboxylate, and solvent molecules. In a second particular set of embodiments, $L^1$ and L (or $L^1$ and $L^2$) are amine or phosphine groups; the remaining L groups are selected from halide atoms; and $X^1$ and $X^2$ are independently selected from halide, carboxylate, and solvent molecules. In a third particular set of embodiments, $L^1$, $L^5$, and $L^6$ are amine or phosphine groups; the remaining L groups are selected from halide, carboxylate, and solvent molecules; and $X^1$ and $X^2$ are independently selected from halide, carboxylate, and solvent molecules. In a fourth particular set of embodiments, $L^1$, $L^2$, $L^3$, $L^5$, $L^6$, and $L^7$ are amine or phosphine groups; the remaining L groups are selected from halide, carboxylate, and solvent molecules; and $X^1$ and $X^2$ are independently selected from halide, carboxylate, and solvent molecules. In a fifth particular set of embodiments, all of the L groups are amine or phosphine groups, and $X^1$ and $X^2$ are independently selected from halide, carboxylate, and solvent molecules.

In the amine groups (i.e., —$NR^1R^2R^3$), $R^1$, $R^2$, and $R^3$ (also referred to as "the R groups") are independently selected from hydrogen atoms and hydrocarbon groups having up to six carbon atoms, wherein the hydrocarbon groups (R) have been described above. In one embodiment, all of $R^1$, $R^2$, and $R^3$ are hydrogen atoms, which correspond to the amine groups being —$NH_3$ groups. In other embodiments, at least one (i.e., one, two, or all) of R, $R^2$, and $R^3$ is a hydrocarbon group. In the case of at least one of $R^1$, $R^2$, and $R^3$ being a hydrocarbon group, the one or more hydrocarbon groups may be independently selected from any of the hydrocarbon groups described above, including linear or branched alkyl or alkenyl, cycloalkyl, cycloalkenyl, and aromatic (e.g., phenyl) groups. Some examples of hydrocarbon-containing amine groups include —$NH_2(CH_3)$, —$NH_2(CH_2CH_3)$, —$NH_2(CH_2CH_2CH_3)$, —$NH_2(C_6H_5)$, —$NH(CH_3)_2$, —$NH(CH_2CH_3)$, —$NH(CH_2CH_2CH_3)_2$, —$NH(C_6H_5)_2$, —$N(CH_3)_3$, —$N(CH_2CH_3)_3$, —$N(CH_2N(CH_2CH_2CH_3)_3$, —$N(CH(CH_3)_2)_3$, and —$N(C_6H_5)_3$, wherein $C_6H_5$ represents a phenyl group.

Within an amine (i.e., —$NR^1R^2R^3$) group, two of $R^1$, $R^2$, and $R^3$ may or may not be (i.e., are optionally) interconnected to form an N-containing ring. The ring is typically a five-, six-, or seven-membered ring. For example, $R^1$ and $R^2$ may be selected as ethyl and n-propyl groups, respectively, which may interconnect at their ends to form a piperidine ring (with simultaneous removal of two hydrogen atoms where the carbon-carbon connection is being made). The possibility also remains that one or both of $R^1$ and $R^2$ may be interconnected at a non-terminating carbon atom, in which case the resulting ring would contain an alkyl substituent. Moreover, if one or both of $R^1$ and $R^2$ are alternatively selected as alkenyl groups, the ring resulting from interconnection of $R^1$ and $R^2$ would contain the respective level of unsaturation. A pyridine ring, in particular, would require all of the $R^1$, $R^2$, and $R^3$ groups on an amine group to interconnect to form the aromatic ring.

In the case where two adjacent groups on a Ru atom (i.e., selected from $L^1$, $L^2$, $L^3$, $L^4$, $L^5$, $L^6$, $L^7$, $L^8$, $X^1$, and $X^2$) are —$NR^1R^2R^3$ groups, the adjacent $R^1$ groups or adjacent $R^2$ groups or adjacent $R^3$ groups (i.e., from adjacent amine groups) may be interconnected to form a bidentate ligand on the Ru atom. For example, two adjacent $R^1$ groups on adjacent amine groups on a Ru atom may be selected as methyl groups, and the methyl groups interconnected to form an ethylenediamine (i.e., $R^2R^3N$—$CH_2CH_2$—$NR^2R^3$) ligand, wherein $R^2$ and $R^3$ are independently selected from hydrogen and hydrocarbon groups, and wherein multiple occurrences of $R^2$ or $R^3$ are independently selected (i.e., two instances of $R^2$ may be the same or different, and the same for $R^3$). In some embodiments, two or three of the R groups within an amine group may interconnect to form an N-containing ring, as described earlier above, and the N-containing ring may further interconnect with an R group of an adjacent amine group on a Ru atom to form a bidentate ligand containing at least one N-containing ring. For example, in some embodiments, two adjacent amine groups on a Ru atom can be taken as pyridine groups (as described earlier above), and the two pyridine rings can be interconnected to form a bipyridine ligand. As a further example, three adjacent amine groups on a Ru atom may each be selected as pyridine groups, and the three pyridine rings interconnected at their 2-positions to form a terpyridine ligand.

In the phosphine groups (i.e., —$PR^5R^6R^7$), $R^5$, $R^6$, and $R^7$ (also referred to as "the R groups") are independently selected from hydrocarbon groups having up to six carbon atoms, wherein the hydrocarbon groups (R) have been described above. The one or more hydrocarbon groups may be independently selected from any of the hydrocarbon groups described above, including linear or branched alkyl or alkenyl, cycloalkyl, cycloalkenyl, and aromatic (e.g., phenyl) groups. Some examples of phosphine groups include —P(CH$_3$)$_3$, —P(CH$_2$CH$_3$)$_3$, —P(CH$_2$CH$_2$CH$_3$)$_3$, —P(CH(CH$_3$)$_2$)$_3$, and —P(C$_6$H$_5$)$_3$, wherein C$_6$H$_5$ represents a phenyl group Within a phosphine (i.e., —PR$^5$R$^6$R$^7$) group, two of R$^5$, R$^6$, and R$^7$ may or may not be (i.e., are optionally) interconnected to form a P-containing ring. The ring is typically a five-, six-, or seven-membered ring, such as described above for the amine groups. In the case where two adjacent groups on a Ru atom (i.e., selected from L$^1$, L$^2$, L$^3$, L$^4$, L$^5$, L$^6$, L$^7$, L$^8$, X$^1$, and X$^2$) are —PR$^5$R$^6$R$^7$ groups, the adjacent R$^5$ groups or adjacent R$^6$ groups or adjacent R$^7$ groups (i.e., from adjacent phosphine groups) may be interconnected to form a bidentate ligand on the Ru atom. For example, two adjacent R$^1$ groups on adjacent phosphine groups on a Ru atom may be selected as methyl groups, and the methyl groups interconnected to form an ethylenediphosphine (i.e., R$^6$R$^7$P—CH$_2$CH$_2$—PR$^6$R$^7$) ligand, wherein R$^6$ and R$^7$ are independently selected from hydrocarbon groups, and wherein multiple occurrences of R$^6$ or R$^7$ are independently selected (i.e., two instances of R$^6$ may be the same or different, and the same for R$^7$). The possibility also exists for a phosphine group to interconnect with an adjacent amine group, i.e., a ligand containing at least one phosphine group and at least one amine group.

Any one or more of the L groups or X groups may be carboxylate groups (R$^4$C(O)O—) provided that at least one of the L and X groups is an amine or phosphine group, wherein R$^4$ is selected from hydrogen atom and hydrocarbon groups having up to six carbon atoms, wherein the hydrocarbon groups (R) have been described above. In some embodiments, one or both of X$^1$ and X$^2$ are carboxylate groups, while the L groups may or may not also include one or more carboxylate groups. In one embodiment, R$^4$ is a hydrogen atom, which results in the carboxylate group being a HC(O)O— (formate) group. In another embodiment, R$^4$ is a hydrocarbon group, such as any of the hydrocarbon groups described above, including linear or branched alkyl or alkenyl, cycloalkyl, cycloalkenyl, and aromatic (e.g., phenyl) groups. Some examples of hydrocarbon-containing carboxylate groups include acetate, propionate, butyrate, valerate, caproate, and benzoate.

For purposes of the invention, each Ru atom is preferably bound to no more than two solvent molecules. Thus, each Ru atom may independently be bound to zero, one, or two solvent molecules. In some embodiments, the Ru atoms are not bound to any solvent molecules, in which case the complex according to Formula (1) has no solvent molecules. In other embodiments, at least one or both of X$^1$ and X$^2$ are solvent molecules, or X$^1$ and X$^2$ are solvent molecules and one L group on each of the Ru atoms may or may not also be solvent molecules. The solvent molecules considered herein are neutral (uncharged) molecules that typically have melting (freezing) points of up to or less than 40, 35, 30, 25, 20, 10, or 0° C. The solvent molecule may be selected from, for example, water (H$_2$O), alcohols (ROH, where scope of R has been provided above), ethers (ROR), amides (R$_2$NC(O)R, where one or more R groups may alternatively be hydrogen atoms), sulfoxides (RS(O)R), nitriles (RCN), and ketones (RC(O)R), wherein multiple R groups in a solvent molecule are independently selected (i.e., may be the same or different) and may or may not interconnect to form a ring. Some examples of alcohol solvents include methanol, ethanol, n-propanol, isopropanol, n-butanol, isobutanol, and phenol; some examples of ether solvents include diethyl ether, tetrahydrofuran, and dimethoxyethane (glyme); some examples of amide solvents include formamide, dimethylformamide, dimethylacetamide, dimethylpropionamide, and N-methylpyrrolidinone; an example of a sulfoxide solvent includes dimethylsulfoxide; some examples of nitrile solvents include acetonitrile and propionitrile; some examples of ketone solvents include acetone, 2-butanone, 2-pentanone, 3-pentanone, and cyclohexanone. For purposes of the invention, the solvent does not include amines (i.e., of the formula NR$^1$R$^2$R$^3$), phosphines (i.e., of the formula PR$^5$R$^6$R$^7$) or acid compounds. Numerous other solvents, including some that are not easily classified, are considered herein, such as hexamethylphosphoramide (HMPA).

Depending on the oxidation state of the Ru atoms and selection of groups bound to the Ru atom s, the inhibitor compound shown in Formula (1) may have an overall positive or negative charge, which necessitates an association with one or more anions or cations (i.e., counter-anions or counter-cations) to establish overall charge neutrality of the compound in Formula (1). Typically, each of the Ru atoms is ascribed a +4 charge and the μ-nitrido linkage is ascribed a −3 charge. In particular embodiments, L$^1$, L$^2$, L$^3$, L$^4$, L$^5$, L$^6$, L$^7$, and L$^8$ are neutral species (e.g., solvent, amine, or phosphine) and X$^1$ and X$^2$ are anionic (e.g., halide or carboxylate), in which case the complex shown in Formula (1) will have a +3 charge (thus requiring association with anionic species providing a −3 charge to make the overall complex charge neutral). In other particular embodiments, L$^1$, L$^2$, L$^3$, L$^4$, L$^5$, L$^6$, L$^7$, L$^8$, X$^1$, and X$^2$ are all neutral species, in which case the complex shown in Formula (1) will have a +5 charge (thus requiring association with anionic species providing a −5 charge to make the overall complex charge neutral). Although not typical, the possibility remains that 5, 6, 7, or 8 of the L and X groups are anionic (e.g., halide and/or carboxylate), in which case the complex shown in Formula (1) will be uncharged (in the case of 5 anionic L and/or X groups) or negatively charged (in the case of 6-8 anionic L and/or X groups). Some examples of counter-anions include halide atoms, carboxylate groups, carbonate, bicarbonate, sulfate, bisulfate, nitrate, borate anions (e.g., tetraphenylborate), perchlorate, carborane anions, tosylate, SO$_3$CF$_3^-$ (i.e., OTf), PF$_6^-$, SbF$_6^-$, and AsF$_6^-$. Some examples of counter-cations include alkali metal ions (e.g., Li$^+$, Na$^+$, K$^+$, and Rb$^+$), alkaline earth metal ions (e.g., Mg$^{+2}$, Ca$^{2+}$, Sr$^{+2}$, and Ba$^{+2}$), ammonium (e.g., tetramethylammonium and tetraethylammonium), and phosphonium (e.g., tetramethylphosphonium, tetraethylphosphonium, and tetraphenylphosphonium).

The ruthenium complexes described herein can be synthesized by any suitable means, including by methodologies and techniques well known in the art. In a preferred embodiment, a typical synthesis starts with a precursor of the formula A$_3$[Ru$_2$(μ-N)Y$_8$(X$^1$)$_2$], where A is a monovalent cation, Y is a halide, and X$^1$ is a solvent molecule (as described above). In particular embodiments, K$_3$[Ru$_2$(μ-N)Cl$_8$(OH$_2$)$_2$] is used as a starting material. The foregoing compound can, in turn be prepared from K$_2$[RuCl$_5$NO]. The synthesis of K$_3$[Ru$_2$(μ-N)Cl$_8$(OH$_2$)$_2$] is described in, for example, Mukaida, *Bull. Chem. Soc. Jap.,* 1970, 43, 3805 and M. J. Cleare et al., *J. Chem. Soc. A,* 1970, 1117, the contents of which are herein incorporated by reference in their entirety. The synthesis of K$_2$[RuCl$_5$NO] is described in, for example, V. A. Emel'yanov et al., *Russ. J. Inorg. Chem.,* 2013, 58, 956 and J. R. Durig et al., *Spectrochim. Acta.,* 1966, 22, 1091-1100, the contents of which are herein incorporated by reference in their entirety. FIG. 1B shows a simplified and generalized synthetic scheme for the preparation of two exemplary compounds of the invention: [Ru$_2$(μ-N)(NH$_3$)$_8$(Cl)$_2$]Cl$_3$ (C-2) and [Ru$_2$(μ-N)(en)$_4$(Cl)$_2$]Cl$_3$ (C-3), where en=ethylenediamine. Notably, some evidence indicates that the foregoing complexes (C-2 and C-3) having X groups as chloride ions undergo substitution or fluxional exchange with water or other solvent molecules when in contact with water or other solvent molecule. When the chloride ions are substituted with water molecules, the foregoing C-2 and C-3 complexes can alternatively be considered as having the following structures: [Ru$_2$(μ-N)(NH$_3$)$_8$(H$_2$O$_2$]Cl$_5$ (C-2) and [Ru$_2$(μ-N)(en)$_4$(H$_2$))$_2$]Cl$_5$ (C-3). For this reason, C-2 and C-3 and other structurally related complexes in which one or both X groups are halide can be considered to also correspond with or be in admixture (e.g., in equilibrium) with the corresponding water-substituted variant.

Generally, any of a variety of diruthenium complexes of the general formula:

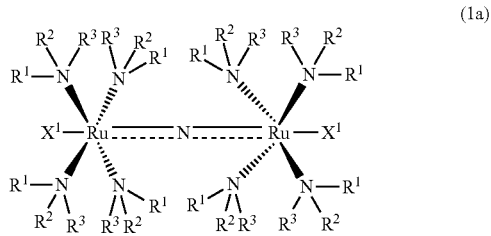

(1a)

can be prepared by reacting K$_3$[Ru$_2$(μ-N)Cl$_8$(X$^1$)$_2$] with the desired amine (NR$^1$R$^2$R$^3$), in which case the amine molecules displace the chloride atoms in the precursor molecule. The X$^1$ groups in Formula (1a) are generally solvent molecules, carboxylate groups, or halide atoms, although one or both of the X$^1$ groups may be amine or phosphine groups, wherein the X$^1$ amine groups may be the same or different than the remainder of the amine groups shown in Formula (1a). In the case of X$^1$ in Formula (1a) being solvent molecules, the complex shown in Formula (1a) possesses a +5 charge, which necessitates a counter-anionic charge of −5 (e.g., 5×Cl$^-$). In the case of X$^1$ in Formula (1a) being carboxylate or halide, the complex shown in Formula (1a) possesses a +3 charge, which necessitates a counter-anionic charge of −3 (e.g., 3×Cl). As an example, the compound [Ru$_2$(μ-N)(NH$_3$)$_8$(H$_2$O)$_2$]Cl$_5$ (C-2) may be synthesized by reacting K$_3$[Ru$_2$(μ-N)Cl$_8$(OH$_2$)$_2$] with ammonia (as described in M. J. Cleare et al., *J. Chem. Soc. A*, 1970, 1117). As another example, the compound [Ru$_2$(μ-N)(en)$_4$((H$_2$O)$_2$]Cl$_5$ (C-3), may be synthesized by reacting K$_3$[Ru$_2$(μ-N)Cl$_8$(OH$_2$)$_2$] with ethylenediamine (e.g., as described in W. P. Griffith et al., *J. Chem. Soc., Dalton Trans.*, 1973, 1315). Analogous compounds can be prepared by reaction of K$_3$[Ru$_2$(μ-N)Cl$_8$(OH$_2$)$_2$] with any other amine, such as described above, e.g., methylamine, dimethylamine, trimethylamine, piperidine, 4-methylpiperidine, azepane, cyclohexylamine, aniline, pyridine, 4-methylpyridine, bipyridine (i.e., 2,2'-bipyridine), 4,4'-dimethyl-2,2'-dipyridine, terpyridine, phenanthroline, and indole (e.g., wherein two, four, six, or eight (all) of the amine groups in Formula (1a) are any of the foregoing amines).

The above exemplary synthetic method can also be applied to the synthesis of phosphine-containing complexes, i.e., where one or more phosphine groups (PR$^5$R$^6$R$^7$) replace one or more amine groups in Formula (1a). Thus, by an analogous process, any of a variety of diruthenium complexes of the general formula:

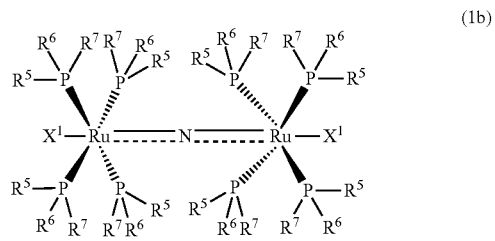

(1b)

can be prepared by reacting K$_3$[Ru$_2$(μ-N)Cl$_8$(X$^1$)$_2$] with the desired phosphine (PR$^5$R$^6$R$^7$), in which case the phosphine molecules displace the chloride atoms in the precursor molecule. The X$^1$ groups in Formula (1b) are generally solvent molecules, carboxylate groups, or halide atoms, although one or both of the X$^1$ groups may be phosphine or amine groups, wherein the X$^1$ phosphine groups may be the same or different than the remainder of the phosphine groups shown in Formula (1b).

In another aspect, the invention is directed to pharmaceutical compositions that contain any of the above-described ruthenium complexes dispersed in a pharmaceutically acceptable carrier, i.e., vehicle or excipient. The complex is dispersed in the pharmaceutically acceptable carrier by either being mixed (e.g., in solid form with a solid carrier) or dissolved or emulsified in a liquid carrier. The pharmaceutical composition may or may not also be formulated together with one or more additional active ingredients or adjuvants that improve the overall efficacy of the pharmaceutical composition, particularly as relates to the treatment of a disease or condition that operates by mitochondrial calcium transport.

The ruthenium complex and carrier may be formulated into pharmaceutical compositions and dosage forms according to methods well known in the art. The pharmaceutical compositions of the present invention may be formulated for administration in liquid or solid form. In different embodiments, the pharmaceutical formulation may be formulated for oral administration (e.g., as tablets, capsules, powders, granules, pastes, solutions, suspensions, drenches, or syrups); parenteral administration (e.g., by subcutaneous, intramuscular or intravenous injection as provided by, for example, a sterile solution or suspension); topical application (e.g., as a cream, ointment, or spray); sublingual or buccal administration; ocular administration; transdermal administration; or nasal administration.

The phrase "pharmaceutically acceptable" refers herein to those compounds, materials, compositions, and/or dosage forms which are, within the scope of sound medical judgment, suitable for administration to a subject. The phrase "pharmaceutically acceptable carrier," as used herein, refers to a pharmaceutically-acceptable vehicle, such as a liquid or solid filler, diluent, carrier, manufacturing aid (e.g., lubricant, talc magnesium, calcium or zinc stearate, or stearic acid), solvent, or encapsulating material, that serves to carry the therapeutic composition for administration to the subject. Each carrier should be "acceptable" in the sense of being compatible with the other ingredients of the formulation and physiologically safe to the subject. Any of the carriers known in the art can be suitable herein depending on the mode of administration.

Some examples of materials that can serve as pharmaceutically-acceptable excipients, particularly for liquid forms, include water; isotonic saline; pH buffering agents; sugars (e.g., lactose, glucose, sucrose, and oligosaccharides, such as sucrose, trehalose, lactose, or dextran); and antimicrobials. Other excipients, more typically used in solid dosage forms, may also be included, e.g., starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

In some embodiments, the carrier further includes a molecular or microscopic (e.g., microscale or nanoscale) sub-carrier in which the complex is loaded, either within and/or conjugated onto the surface of the sub-carrier. The sub-carrier can be composed of, for example, a biocompatible and biodegradable polymer, e.g., based on a polyhydroxyacid biopolyester or polysaccharide. The overall structure of the sub-carrier can be, a micelle, a liposome, dendrimer, nanoparticle, or porous scaffold. These and numerous other types of sub-carriers are well known in the art. The sub-carrier may function to protect the complex during transit, e.g., while in the bloodstream or while passing through the gastrointestinal tract, to release the complex closer to the target cells with lower chance of degradation. The sub-carrier may also be functionalized with one or more targeting agents that selectively target a class of cells to be treated with the complex. In particular embodiments, the targeting agent selectively targets mitochondria or the MCU itself. The targeting agent can be, for example, an antibody, antibody fragment, siRNA, or small molecule receptor binder.

In another aspect, the invention is directed to a method for treating or preventing a disease or condition that operates by calcium transport through the mitochondrial calcium uniporter (MCU) in a subject having (or at risk of) such disease or condition. The condition being treated or prevented may be, for example, reperfusion injury (e.g., in cardiac or brain tissue), such as may occur after an ischemic event. In some embodiments, the reperfusion injury occurs in brain tissue associated with a stroke. In other embodiments, the reperfusion injury is associated with organ transplantation. In the method, any of the above described ruthenium complexes, typically as a pharmaceutical formulation, is administered to the subject in a pharmaceutically effective amount that effectively inhibits the MCU to the extent that the disease or condition is treated or prevented. In some embodiments, the method prevents reperfusion injury in bodily tissue by administering the inhibiting compound after an ischemic event and before or during reperfusion of oxygen to the bodily tissue. The method may also treat reperfusion injury by resulting in at least partial restoration of bodily tissue that has been damaged by an ischemic event followed by reperfusion injury. Mitochondrial calcium overload has also been implicated in traumatic brain injury (TBI), e.g., G. Cheng et al., *British Journal of Pharmacology*, 167(4), 699-719, October 2012, the contents of which are incorporated herein in their entirety. Thus, the method may also treat, prevent, or mitigate any of the known forms of TBI. In some embodiments, the method results in protection of the brain during or after TBI. The TBI may also be classified as mild, moderate, or several TBI. Mitochondrial calcium overload has also been implicated in spinal cord injury (SCI), e.g., N. E. Scholpa et al., *J Pharmacol. Exp. Ther.,* 363(3), 303-313, December 2017, the contents of which are incorporated herein in their entirety. Thus, the method may also treat, prevent, or mitigate any of the known forms of SCI, including primary and secondary phases of SCI.

The mode of administration may be any of the modes of administration described above. A typical mode of administration for purposes of the present invention is by intravenous injection. In one embodiment, the ruthenium complex is injected into the bloodstream, in which case the complex is systemically distributed through the body. In another embodiment, the complex is injected locally directly into or in the vicinity of biological tissue having (or at risk of) the condition being treated or prevented, particularly reperfusion injury.

In the treatment or prevention method, the ruthenium complex is administered in a therapeutically effective amount. The therapeutically effective amount of the compound to be administered can be readily determined according to methods familiar to physicians and clinicians, e.g., during pre-clinical and clinical trials. As is well known in the art, the dosage of the active ingredient(s) depends not only on the disease or condition being treated, but the method of administration, size of the patient, and potential side effects. Dosing is dependent on the severity and responsiveness of the disease or condition being treated or prevented, with the course of treatment or prevention lasting from several days to several months, or until a cure is effected or a diminution of the disease state is achieved. Optimal dosing schedules can be calculated from measurements of drug accumulation in the body of the patient. The administering physician can determine optimum dosages, dosing methodologies, and repetition rates. In different embodiments, depending on these and other factors, a suitable dosage of the active ingredient may be precisely, at least, or no more than, for example, 1 mg, 10 mg, 50 mg. 100 mg, 200 mg, 300 mg, 400 mg, 500 mg, 600 mg, 700 mg, 800 mg, 900 mg, 1000 mg, 1200 mg, or 1500 mg, per 50 kg, 60 kg, or 70 kg adult, or a dosage within a range bounded by any of the foregoing exemplary dosages. Depending on these and other factors, the composition is administered in the indicated dosage by any suitable schedule, e.g., once, twice, or three times a day for a total treatment time of one, two, three, four, or five days, and up to, for example, one, two, three, or four weeks or months. The indicated dosage may alternatively be administered every two or three days, or per week. Alternatively, or in addition, the composition is administered until a desired change is evidenced.

The composition according to Formula (1) can be co-administered with one or more other therapeutic agents outside the scope of Formula (1). In a first instance, the co-administration is accomplished by including a complex of Formula (1) in admixture with one or more other therapeutic agents in the same pharmaceutical composition being administered. In a second instance, the co-administration can be accomplished by administering a complex of Formula (1) separately from one or more other therapeutic agents, i.e., at the same time or at different times. In some embodiments, the one or more other therapeutic agents function to desirably modulate or work in synergy with a ruthenium complex under Formula (1). The one or more other therapeutic agents may be selected from, for example, any of the conventional MCU inhibitors known in the art, such as Ru360 or DS16570511, the latter of which is described in, for example, N. Kon et al., *Cell Death Discov.*, 3, 17045 (2017).

Examples have been set forth below for the purpose of illustration and to describe the best mode of the invention at the present time. However, the scope of this invention is not to be in any way limited by the examples set forth herein.

EXAMPLES

Preparation of Complexes

The nitrido-bridged ruthenium complexes, which bear a linear Ru—N—Ru core, can be readily accessed via ligand substitution reactions by using the precursor complex $K_3[Ru_2(\mu-N)Cl_8(OH_2)_2]$ (e.g., J. Urgiles, *Dalt. Trans.* 2017, 46, 14256-14263). Accordingly, the reaction of this complex anion with either aqueous ammonium hydroxide or ethylenediamine (en) afforded the compounds $[Ru_2(\mu-N)(NH_3)_8Cl_2]Cl_3$ (Ru265; referred to herein as C-2) and $[Ru_2(\mu-N)(en)_4Cl_2]Cl_3$ (C-3) (shown in FIG. 1B). In contrast to the low-yielding synthesis of Ru360 and related analogues, the syntheses of the μ-nitrido compounds proceeded in moderate yield and does not require tedious chromatographic purification. These compounds were fully characterized by NMR, IR, UV-Vis spectroscopy, and single-crystal X-ray diffraction. UV-Vis spectra reveal strong charge transfer bands at 265 nm ($\varepsilon=34,000\pm2000$ $M^{-1}$ $cm^{-1}$) and 273 nm ($\varepsilon=29,000\pm4000$ $M^{-1}$ $cm^{-1}$) for C-2 and C-3, respectively, with a lower energy shoulder observed near 325 nm for both complexes. IR spectroscopy revealed distinct bands near 1050 $cm^{-1}$, corresponding to the asymmetric Ru—N—Ru vibrational mode. Furthermore, $^1H$ and $^{13}C\{^1H\}$ NMR spectroscopy showed relatively sharp signals for the $NH_3$ and ethylenediamine ligands, confirming the diamagnetic character of the $Ru^{IV}/Ru^V$ system.

Single-crystal X-ray crystallography was employed to fully elucidate the three-dimensional structures of C-2 and C-3. X-ray diffraction quality crystals of C-2 and C-3 were grown by vapor diffusion of dioxane into water and vapor diffusion of ethanol into dilute hydrochloric acid, respectively. These structures verify the presence of both the linear Ru—N—Ru motif ($C-2_{Ru-N-Ru}=180°$; $C-3_{Ru-N-Ru}=176.3°$) and the chloride axial ligands. The Ru—N distances of the nitrido bridge agree well with previously synthesized compounds (e.g., J. Urgiles, supra). The $NH_3$ ligands of the bridged $Ru^{IV}$ centers of C-2 are arranged in an eclipsed configuration, whereas the ethylenediamine ligands of C-3 crystallize in a staggered conformation. This disparity may indicate that the rotation about the Ru—N—Ru axis is facile.

1. Preparation of $[Ru_2(\mu-N)(NH_3)_8(Cl)_2]Cl_3$ (C-2)

In a typical procedure, 288 mg (0.440 mmol) of $K_3[Ru_2(\mu-N)Cl_8(OH_2)_2]$ was dissolved in 100 mL of concentrated aqueous ammonia (d=0.88, 18 M) in a thick-walled pressure flask with a teflon screw cap. The vessel was closed, and the solution was heated at 75° C. for 6 hours to yield a turbid orange solution. (Caution: The pressure vessel becomes pressurized, and the reaction should be performed in a ventilated fume hood behind a blast shield). After cooling, the orange-brown precipitate was removed by filtration and the filtrate was evaporated under reduced pressure. The resulting yellow-white solid was dissolved in 30 mL of boiling water and precipitated with the addition of 9 mL of concentrated HCl (14 M) and cooling to 0° C. The peach-colored precipitate was collected by vacuum filtration and washed with 6 M HCl (10 mL), cold water (10 mL), and acetone (10 mL). The solid was purified by re-precipitating from boiling water with more acid and cooling. The pure product was collected by vacuum filtration and washed with 6 M HCl (20 mL), ice cold water (10 mL), acetone (10 mL), and diethylether (10 mL) followed by removal of residual solvent in vacuo. In some cases, multiple precipitations with HCl were required to obtain pure product. Yield: 95.7 mg (0.169 mmol, 38.4%). NMR (500 MHz, $d_6$-DMSO) $\delta(ppm)=4.15$ ($NH_3$). IR (KBr, $cm^{-1}$): 3438 (m), 3272 (s, br), 1609 (m), 1297 (s, sh), 1046 (m, sh), 834 (m, br), 794 (w), 740 (w) UV-vis ($\varepsilon$, $M^{-1}$ $cm^{-1}$)=232 nm (9800±1300), 265 nm (34000±2000), 322 nm (1400±120). Elemental analysis: Calculated (%, for $H_{24}Cl_5N_9Ru_2 \cdot 2H_2O$): C, 0; H, 4.99; N, 22.29; Cl, 31.33; Ru, 35.73. Found (%) C, 0.2; H, 4.83; N, 22.79; Cl, 31.33; Ru, 35.75.

II. Preparation of $[Ru_2(\mu-N)(en)_4(H_2O)Cl_2]Cl_5$ (C-3)

100 mg (0.153 mmol) of $K_3[Ru_2(\mu-N)Cl_8(OH_2)_2]$ was suspended in 1 mL of distilled water and heated to boiling. Ethylene diamine (1 mL; 14.95 mmol) was separately heated in 1 mL of distilled water and heated to boiling before being added to the ruthenium suspension. The mixture was heated to reflux for 3 hours. The resulting orange solution was cooled to room temperature before 9 mL of concentrated (12 M) HCl was added and the solution was further cooled to 0° C. The orange precipitate was collected by filtration, re-precipitated from hot aqueous solution using concentrated 1-HCl, and washed with 6M HCl (10 mL), water (10 mL), and acetone (10 mL), before drying under vacuum. Yield: 27.3 mg (0.043 mmol; 28%). $^1H$ NMR (500 MHz, $D_2O$) (ppm)=5.41 (d, J=75 Hz, 16H), 3.28 (s, 8H), 2.85 (s, 8H). $^{13}C\{^1H\}$ NMR (125 MHz, $D_2O$)) $\delta(ppm)=$ 45.96. R (KBr) v ($cm^{-1}$)=3477 (m), 3427 (m), 3276 (s), 3181 (s), 3071 (s), 2948 (s), 1637 (w), 1589 (s), 1442 (in), 1323 (m), 1273 (m), 1138 (s), 1098 (s), 1056 (s), 989 (s), 881 (w), 797 (w), 752 (w) 708 (w), 695 (w), 548 (w), 446 (w). UV-vis ($\varepsilon$, $M^{-1}$ $cm^{-1}$)=240 nm (8600±560), 270 nm (29000±2100), 325 nm (1800±100). Elemental analysis: Calculated (%, for $H_8C_8Cl_5N_9Ru_2 \cdot 2.5H_2O$): C, 14.15; H, 5.49; N, 18.57. Found (%) C, 14.20; H, 5.26; N, 18.19.

Mitochondrial $Ca^{2+}$ Uptake Inhibition and Cell Permeability

Cell Culture.

HEK293 (human embryonic kidney cells were obtained from American Type Culture Collection (ATCC, Washington D.C.) and cultured as adherent monolayers in a humidified 5% $CO_2$ atmosphere at 37° C. in Minimum Essential Media supplemented with 10% fetal bovine serum (FBS) and 100 U/mL penicillin/streptomycin. HeLa cells were cultured in Dulbecco's Modified Eagle's Medium (DMEM) supplemented with 10% FBS and 100 U/mL penicillin/streptomycin. Cells were checked for contamination monthly using the PlasmoTest™ mycoplasma detection kit. Ventricular cardiomyocytes were isolated from neonatal rats (NRVMs) as previously described (H. M. Piper et al., Piper H. M. (eds), Cell Culture Techniques in Heart and Vessel Research, Springer Verlag: Berlin, 1990). The isolated myocytes were cultured in Ham's F-10 supplemented with 5%/o fetal bovine serum (FBS) and penicillin/streptomycin (100 U/ml) at 37° C. in a 95% air/5% $CO_2$ humidified atmosphere for four days Cytotoxicity Measurements.

Cells were seeded at 4000 cells/well in 100 μL/well in a 96-well plate and incubated for 24 hours. The media was removed and replaced with 200 μL of growth media containing varying concentrations of the complex. After 72 hours of incubation, the media was replaced with MEM containing 1 mg/mL of (4,5-dimethylthiazol-2-yl)-2,5-dipheyltetrazolium bromide (MTT). After four hours incubation, the media was removed and the purple formazan crystals were solubilized using 100 µL of a 8/1 DMSO/glycine buffer (pH 10) mixture. The absorbance at 570 nm was measured using a plate reader.

Measurement of MCU-mediated $Ca^{2+}$ uptake and $\Delta\Psi_m$ in permeabilized cells.

An equal number of IHEK293T ($6\times10^6$ cells) were washed in $Ca^{2+}$ free PBS, pH 7.4, resuspended and permeabilized with 40 µg/ml digitonin in 1.5 ml of intracellular medium (ICM) composed of 120 mM KCl, 10 mM NaCl, 1 mM K—$H_2PO_4$, 20 mM HE PES-Tris, pH 7.2 and 2 µM thapsigargin to block the SERCA pump. All measurements were performed in the presence of 2 mM succinate. The permeabilized cells were loaded with JC-1 (800 nM) and Fura2-FF (0.5 µM), respectively. Fluorescence was monitored in a multi-wavelength excitation dual-wavelength emission fluorimeter. $[Ca^{2+}]_{out}$ is represented as the excitation ratio (340 nm/380 nm) of Fura2-FF/FA fluorescence and $\Delta\Psi_m$ as the ratio of the fluorescence of J-aggregate (570 nm excitation/595 nm emission) and monomer (490 nm excitation/535 nm emission) forms of JC-1. A series of extra-mitochondrial $Ca^{2+}$ bolus (20 µM) was added and mitochondrial uncoupler, CCCP (2 juM), were added at the indicated time points. All of the experiments were performed at 37° C. with constant stirring.

Whole Cell Uptake.

HEK293 cells were grown to near confluence in 75 cm$^2$ dishes. On the day of the experiment, the culture media was removed, and the cells were washed with 1 mL PBS. The cells were then treated with culture media containing 50 µM of the complex and incubated at 37° C. for 24 hours. The cells were washed with 1 mL of PBS and harvested using 0.05% trypsin. The cells were pelleted by centrifugation, re-suspended in 1 mL of PBS, and pelleted again. The washing and pelleting step was repeated a total of three times, after which the supernatant was removed and the cells were suspended in 500 µL of lysis buffer containing 1% w/v 3-[3-cholamidopropyl)dimethylammonio]-1-propane-sulfonate) (CHAPS), 5 mM ethylenediamine tetraacetic acid (EDTA), and 50 mM tris(hydroxymethyl)aminomethane (Tris) and 100 mM NaCl (pH=7.4). The suspension was vortexed for 30 seconds and incubated on ice for 45 minutes. Control cells not treated with the complexes were handled identically to the treated cells to correct for ruthenium present in the cells, and control dishes were incubated with the complex in the absence of cells to correct for non-specific adsorption of ruthenium to the plastic. If needed, samples were stored in −80° C. until analysis. Ruthenium and protein content of the lysates were determined as described above. Results are reported as the average mass ratio of total ruthenium to protein (pg/µg) in each sample±SEM of three independent trials.

Mitochondrial Isolation Protocol.

Mitochondrial isolation was performed by a modification of previously reported protocols (N. Neman et al., Cell Calcium 2018, 74, 86-93, and J. M. Baughmann et al., Nature 2011, 476, 341-345). Approximately $1\times10^6$ HeLa cells were seeded in 75 cm$^2$ dishes and allowed to adhere overnight. The following day, the cell culture media was removed, and the cells were washed with 3 mL of PBS before treatment with media containing 50 µM of the complex. After 24 hours, the culture media was removed, and the cell monolayer was washed with 3 mL of PBS before the cells were harvested by trypsinization. The cell suspension was centrifuged, and the resulting pellet was resuspended in 3 ml, of PBS and centrifuged again to remove extracellular ruthenium. This washing step was repeated a total of three times. The cell pellet was then suspended in 500 µL of mitochondria isolation buffer containing 200 mM mannitol, 68 mM sucrose, 50 mM piperazine-N,N'-bis(2-ethanesulfonic acid) (PIPES), 50 mM KCl, 5 mM EGTA, 2 mM $MgCl_2$, 1 mM dithiothreitol (DTT), and 1:500 v/v protease inhibitor cocktail (pH=7.4) and was incubated on ice for 20 minutes. The resulting suspension was homogenized by 35 passes through a 25-gauge needle using a 1 mL syringe. The homogenized suspension was centrifuged at 150 g for 5 minutes. The supernatant was transferred to a clean vial and centrifuged for 10 minutes at 14,000 g; and the remaining solid containing other cell organelles and the cell membrane were lyophilized overnight before digestion in 1 mL of tetramethylammonium hydroxide (TMAH; 25% in water) following literature procedures (K. Mallilankaraman et al., Cell 2012, 151, 630-644). The pelleted mitochondria were suspended in 500 µL of water and lysed by sonication. The ruthenium concentration in each sample was determined by GFAAS and was normalized to the protein content of the lysate, which was determined using the Bicinchoninic Acid Protein Assay Kit. Samples that were digested with TMAH were diluted to 2.5% TMAH with water prior to analysis. Results were calculated as the mass ratio of total ruthenium to protein (pg/µg) in each sample±standard deviation of three independent trials. Each replicate for C-2 and C-3 consisted of cells combined from four 75 cm$^2$ dishes. Experiments using C-1 consisted of cells combined from five 75 cm$^2$ dishes to account for low cell permeability.

Measurement of Cytoplasmic and Mitochondrial $Ca^{2+}$ Dynamics in Intact Cells.

HeLa cells were loaded with Fluo-4-AM (5 µM; 30 min) and Rhod-2 AM (2 µM; 50 min) in extracellular medium as previously described (F. Perocchi et al, Nature 2010, 467, 291-296). Coverslips were mounted in an open perfusion microincubator at 37° C. and imaged. After 1 minute of baseline recording, histamine (100 µM) was added, and confocal images were recorded every 3 seconds at 488 and 561 nm excitation using a 40× oil objective. Images were analyzed and quantified by using ImageJ (NIH).

Measurement of Cytoplasmic and Mitochondrial $Ca^{2+}$ Dynamics in Intact Cells with RGECO and GCamP6-mt.

HeLa cells were transiently transfected with genetically encoded cytosolic and mitochondrial targeted $Ca^{2+}$ sensors R-GECO1 and GCamP6-mt plasmids. After 48 hours, the transfected cells were treated with MCU inhibitors (C1, C-2, and C-3; 50 µM). After 1 minute of baseline recording, histamine (100 µM) was added, and the change of R-GECO1 and GCamP6-mt fluorescence was measured with 488-nm and 561-nm excitation on a confocal microscope equipped with a 40× oil objective. Images were analyzed and quantified by using ImageJ (NIH).

Hypoxia/Reoxygenation Exposure.

Freshly isolated NRVMs were subjected to 16 hours of hypoxia (5% $O_2$-5% $CO_2$) followed by 8 hours of reoxygenation (20% $O_2$-5% $CO_2$). To study the protective effect of C-2, HIR was induced in NRVMs pretreated with or without C-2 (50 µM).

Simultaneous measurement (of $Ca^{2+}$ uptake and $\Delta\Psi_m$ in NRVMs.

An equal number of NRVMs ($6\times10^6$ cells) were washed in $Ca^{2+}$ free PBS, pH 7.4, resuspended and permeabilized with 40 µg/ml digitonin in 1.5 mL of intracellular medium (ICM) composed of 120 mM KCl, 10 mM NaCl, 1 mM $KH_2PO_4$, 20 mM Hepes-Tris, pH 7.2 and 2 µM thapsigargin to block the SERCA pump. All measurements were performed in the presence of 2 mM succinate. The simultaneous measurement of mitochondrial membrane potential ($\Delta\Psi_m$) and extra-mitochondrial $Ca^{2+}$ ($[Ca^{2+}]$) clearance were measured as above by using the JC-1 and Fura2-FF dyes. A series of extra-mitochondrial $Ca^{2+}$ bolus (10 µM) was added and mitochondrial uncoupler, CCCP (2 µM), were added at the indicated time points. All the experiments were performed at 37° C. with constant stirring.

Mitochondrial Swelling Assay.

NRVMs were homogenized in ice-cold mitochondrial isolation buffer (10 mM sucrose, 200 mM mannitol, 5 mM HEPES, and 1 mM EGTA, pH 7.4) containing 1 mg/mL fatty acid-free bovine serum albumin. The homogenate was centrifuged for 10 minutes at 1000×g, and the supernatant was centrifuged again at 14,000×g for 10 minutes. The mitochondrial pellets were washed twice and centrifuged at 11,200×g. The isolated mitochondria (1 mg protein) were added to 0.2 mL of buffer mitochondrial swelling buffer (70 mM sucrose, 230 mM mannitol, 3 mM HEPES, 2 mM Trisphosphate, 5 mM succinate). Mitochondrial swelling was measured by decrease in absorbance at 540 nm after addition of $Ca^{2+}$ (250 µM). To study the protective effect of C-2 and Ru360, mitochondrial swelling assay was performed in mitochondria treated with or without the compounds (50 µM).

Elucidation of MCU-Inhibitory Properties of Ruthenium Compounds

With the new nitrido-bridged ruthenium compounds C-2 and C-3 prepared, MCU-inhibitory properties of these compounds were evaluated and their activities compared to C-1, the oxo-bridged Ru360 analogue of the conventional art (S. R. Nathan et al., *Inorg. Chem.* 2017, 56, 3123-3126 and S. R. Nathan et al., *J. Vis. Exp.* 2017, 56527). The cytotoxicity of the complexes in HEK293 cells was first measured using the colorimetric thiazolyl blue tetrazolium bromide (MTT) assay, as well known in the art. This assay revealed that C-2 and C-3 are effectively non-toxic, as indicated by their $IC_{50}$ values of 195±8 µM and 226±19 µM, respectively. To measure the effect of these compounds on MCU activity, permeabilized HEK293T cells were treated with commercially available Ru360, C-1, C-2, or C-3 (5 µM) 200 seconds prior to the delivery of a 20 µM bolus of $Ca^{2+}$ in the presence of 2 mM succinate as an energy source and the sarco/endoplasmic reticulum $Ca^{2+}$-ATPase (SERCA) pump blocker thapsigargin to prevent ER $Ca^{2+}$ uptake (S. Shanmughapriya et al., *Sci. Signal.* 2015, 8, ra23).

Figure 2A:
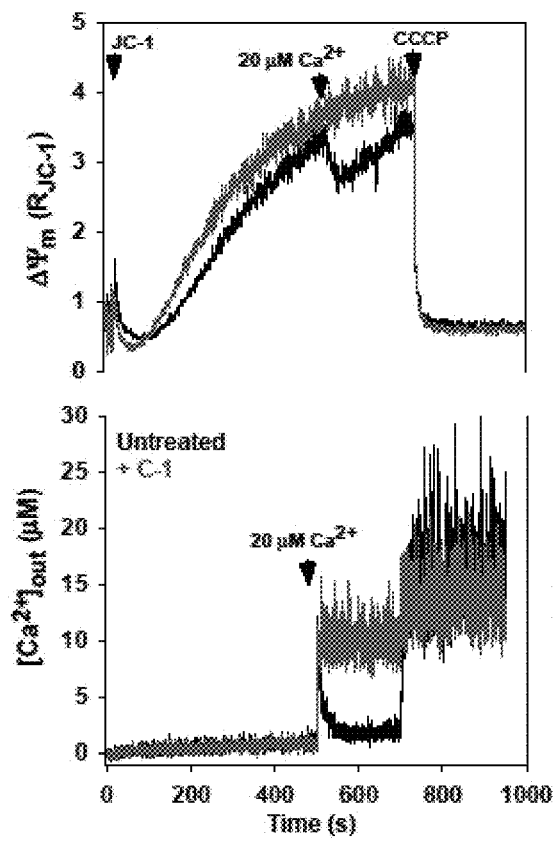
FIGS. 2A-2C are graphs showing changes in mitochondrial membrane potential, $\Delta\Psi_m$ (JC-1, top panel), and extra-mitochondrial $Ca^{2+}$ ($[Ca^{2+}]_{out}$) clearance (Fura-2 FF, bottom panel) in digitonin permeabilized HEK293T cells in response to 20 µM of $Ca^{2+}$ after treatment with 5 µM of C-1 (FIG. 2A), C-2 (FIG. 2B), and C-3 (FIG. 2C). The transient drop in $\Delta\Psi_m$ in control cells upon $Ca^{2+}$ addition indicates accumulation of $Ca^{2+}$ in the mitochondrial matrix.
Figure 2B:
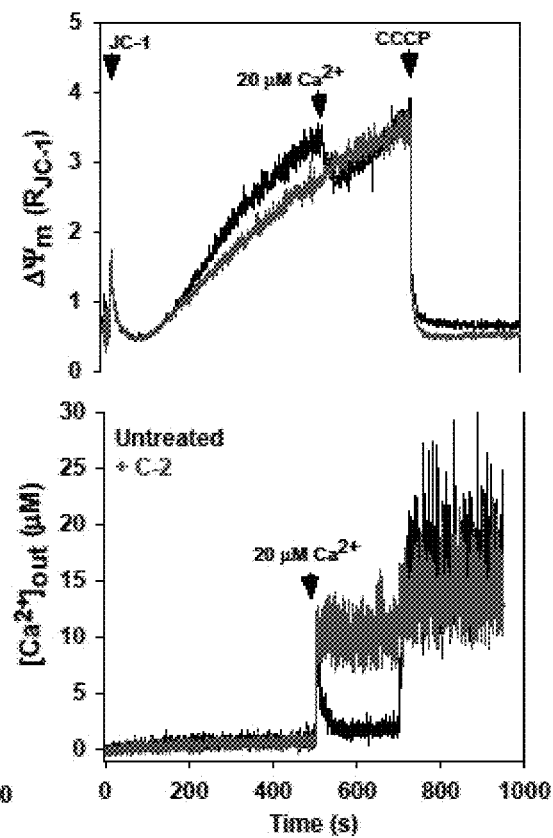
Figure 2C:
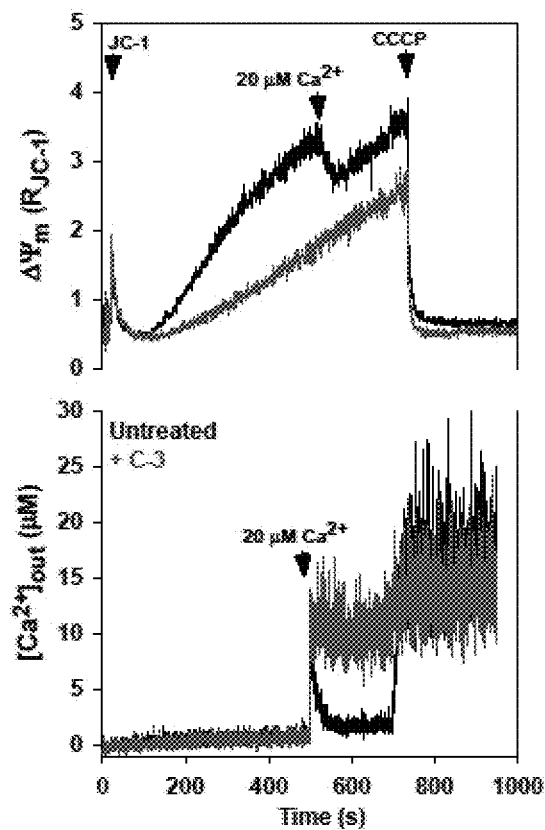
Figure 2D:
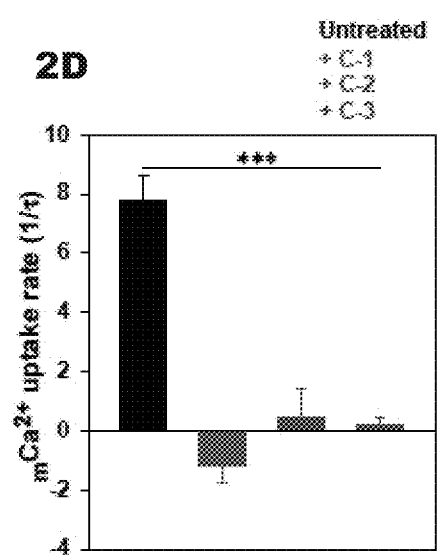
FIG. 2D is a graph quantifying the rate of $[Ca^{2+}]_m$ uptake as a function of decrease in $[Ca^{2+}]_{out}$ after a 20 µM $Ca^{2+}$ pulse.

FIGS. 2A-2C are graphs showing changes in mitochondrial membrane potential ($\Delta\Psi_m$, JC-1, top panel) and extramitochondrial $Ca^{2+}$ ($[Ca^{2+}]_{out}$) clearance (Fura-2 FF, bottom panel) in digitonin permeabilized HEK293T cells in response to 20 µM of $Ca^{2+}$ after treatment with 5 µM of C-1 (FIG. 2A), C-2 (FIG. 2B), and C-3 (FIG. 2C). The transient drop in $\Delta\Psi_m$ in control cells upon $Ca^{2+}$ addition indicates accumulation of $Ca^{2+}$ in the mitochondrial matrix. FIG. 2D is a graph quantifying the rate of $[Ca^{2+}]$ uptake as a function of decrease in $[Ca^{2+}]_{out}$ after a 20 ML $Ca^{2+}$ pulse. Data are represented as mean±standard error of measurement (SEM); ***p<0.001; n=3-6 Extra-mitochondrial $Ca^{2+}$ ($[Ca^{2+}]_o$) was observed to be rapidly cleared in control cells as $Ca^{2+}$ ions were sequestered in the mitochondria by the MCU. In contrast, cells that were treated with C-1, C-2, C-3, (FIGS. 2A-2D) and commercially available Ru360 showed a significant reduction in MCU mediated $_mCa^{2+}$ uptake (FIGS. 2A-2D). Additionally, $\Delta\Psi_m$ was monitored using 5,5',6,6'-tetrachloro-1,1',3,3'-tetraethylbenzimidazolylcarbocyanine iodide (JC-1) dye (M. Reen et al., *Biochemistry* 1991, 30, 4480-4486). Cells treated with commercially available Ru360, C-1, C-2, or C-3 showed no transient A m loss, (FIGS. 2A-2C), a phenomenon that occurs when $Ca^{2+}$ rapidly enters the mitochondria ((K. Mallilankaraman et al., *Cell* 2012, 151, 630-644). These results show that commercially available Ru360, C-1, C-2, and C-3 are all capable of inhibiting MCU-mediated $_mCa^{2+}$ uptake in permeabilized cells without negatively affecting the $\Delta\Psi_m$, thus preserving normal cell function.

Next, the cell permeability of the compounds and their ability to inhibit MCU activity in intact cells was investigated. The cellular uptake of C-1, C-2 and C-3 was quantified as previously described (A. P. King et al., *Inorg. Chem.* 2017, 56, 6609-6623). HEK293 or HeLa cells were incubated with the complexes (50 µM) in culture media for 24 hours before the cells were harvested and lysed. The amount of ruthenium in the cell lysate was determined using graphite furnace absorption spectroscopy (GFAAS) and was normalized to the protein content of each sample. C-2 was observed to be taken up 10 times more effectively than C-1 and over twice as effectively as C-3 in HEK293 cells and twice as effectively as C-1 and C-3 in HeLa cells. To determine the abilities of the complexes to accumulate in the mitochondria, HeLa cells were treated with C-1, C-2 or C-3 (50 µM) in culture media for 24 hours, and the mitochondria were isolated following modified literature procedures (e.g., A. C. Komor et al., *J. Am Chem. Soc.* 2012, 134, 19223-19233). Both the mitochondrial and extramitochondrial fractions were analyzed for ruthenium content. Cells treated with C-1, C-2, or C-3 unexpectedly showed 2-4 times greater uptake of ruthenium into the mitochondria compared to the rest of the cell, which demonstrates the high selectivity of these compounds for the mitochondria. Consistent with the cellular uptake studies, greater than three-fold higher concentrations of C-2 are found in the mitochondria, compared to C-1 and C-3.

Encouraged by the high cell permeability and mitochondrial selectivity of C-2, the capability of this complex to inhibit MCU-mediated $_mCa^{2+}$ uptake in intact, non-permeabilized cells was investigated Briefly, HeLa cells were loaded with the cytosolic calcium concentration ($[Ca^{2+}]$) indicator Fluo-4 AM and the mitochondrial calcium concentration ($[Ca^{2+}]_c$) indicator Rhod-2 AM in the presence or absence of C-1, C-2, and C-3 (50 µM). Cells were stimulated with the GPCR agonist histamine (100 µM) to rapidly elevate $_cCa^{2+}$ levels to induce $_mCa^{2+}$ uptake (Z. Dong et al., *Mol. Cell* 2017, 65, 1014-1028).

Figure 3A:
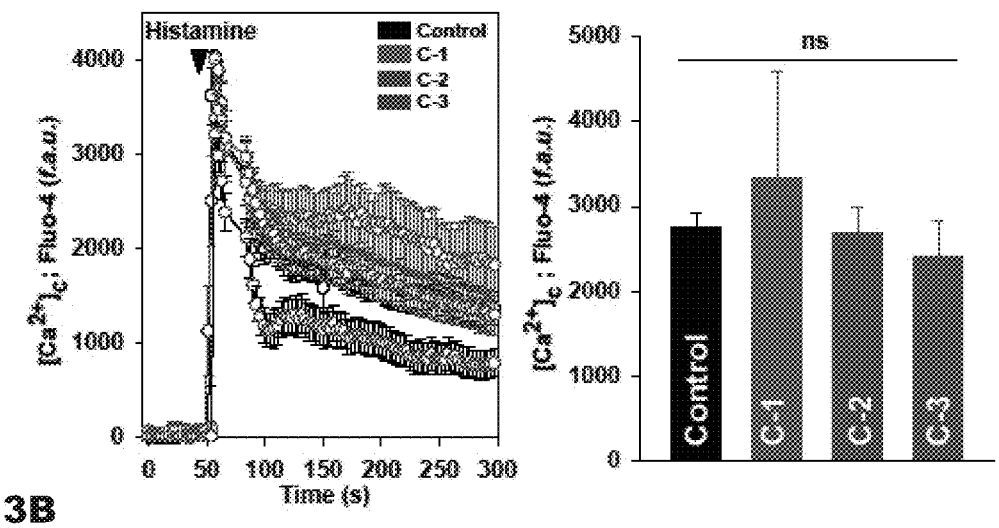
FIGS. 3A and 3B are graphs showing results of cytosolic ($[Ca^{2+}]_c$, Fluo-4 AM) and mitochondrial ($[Ca^{2+}]_m$, Rhod-2 AM) calcium transients in HeLa cells after treatment with histamine (100 µM) that were pretreated with or without C-1, C-2, or C-3 (50 µM) for 30 minutes. The left panels in FIGS. 3A and 3B show the dynamic fluorescence response of the cells upon treatment with histamine, a compound that stimulates mitochonidral calcium uptake. The fluorescence levels (y-axis) signify the amount of calcium detected in either the cytosol (FIG. 3A) or mitochondria (FIG. 3B). The right panels in FIGS. 3A and 3B plot the total calcium levels in the cytosols (FIG. 3A) and mitochondria (FIG. 3B) after equilibration.
Figure 3B:
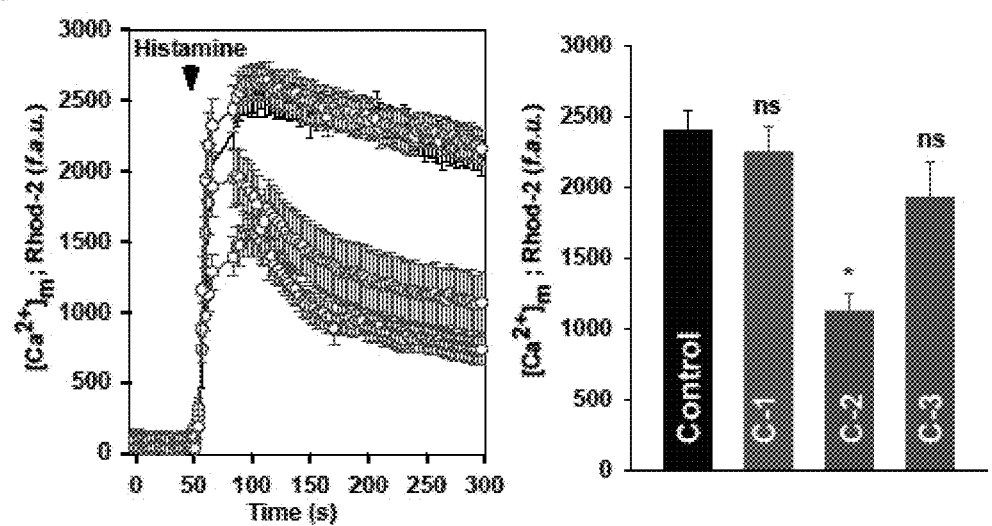
Figure 3C:
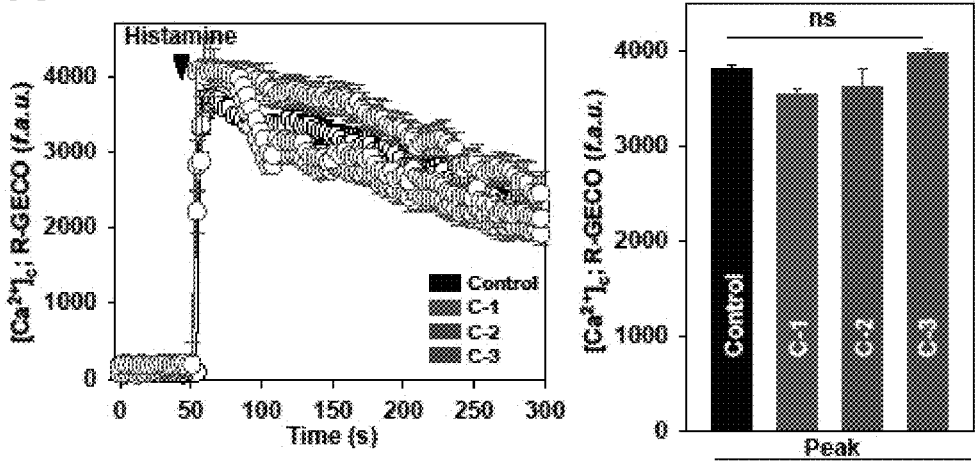
FIGS. 3C and 3D are graphs showing results of cytosolic ($[Ca^{2+}]c$, R-GECO) and mitochondrial ($[Ca^{2+}]_m$, GCamP6-mt)) calcium transients in HeLa cells after treatment with histamine (100 µM) that were pretreated with or without C-1, C-2, or C-3 (50 µM) for 30 minutes. The left panels in FIGS. 3C and 3D show the dynamic fluorescence response of the cells upon treatment with histamine, a compound that stimulates mitochonidral calcium uptake. The fluorescence levels (y-axis) signify the amount of calcium detected in either the cytosol (FIG. 3C) or mitochondria (FIG. 3D). The right panels of FIGS. 3C and 3D plot the total calcium levels in the cytosols (FIG. 3C) and mitochondria (FIG. 3D) after equilibration.
Figure 3D:
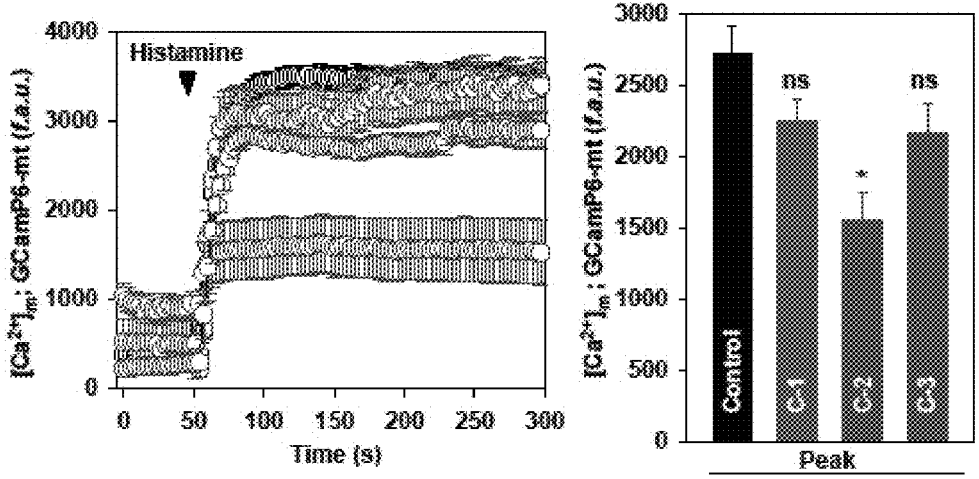

FIGS. 3A and 3B are graphs showing results of cytosolic ($[Ca^{2+}]_e$, Fluo-4 AM) and mitochondrial ($[Ca^{2+}]_m$, Rhod-2 AM) calcium transients in HeLa cells after treatment with histamine (100 µM) that were pretreated with or without C-1, C-2, or C-3 (50 µM) for 30 minutes. FIGS. 3C and 3D are graphs showing results of cytosolic ($[Ca^{2+}]_e$, R-GECO) and mitochondrial ($[Ca^{2+}]_m$, GCamP6-mt)) calcium transients in HeLa cells after treatment with histamine (100 µM) that were pretreated with or without C-1, C-2, or C-3 (50 µM) for 30 minutes. HeLa cells were co-transfected with R-GECO1 and GCamP6-mt. 48 hours post-transfection. Data are represented as mean±SEM. *p<0.05. n=3-6. As shown in FIGS. 3A and 3B, cells treated with C-2 unexpectedly showed significant inhibition of MCU-mediated $_mCa^{2+}$ uptake compared to untreated cells. As shown in FIGS. 3C and 3D, these results were further confirmed using genetically encoded cytosolic (RGECO) and mitochondrial (GCamP6-mt) $Ca^{2+}$ sensors (Y Zhao et al., *Science* 2011, 333, 1888-1891). In contrast, intact cells treated with C-1 or C-3 did not show appreciable inhibition of $_mCa^{2+}$ uptake.

These results are consistent with the results of the cell uptake and MCU $Ca^{2+}$ uptake experiments, which suggests that C-2 is capable of inhibiting $_mCa^{2+}$ uptake in intact cells as a result of its enhanced permeability compared to C-1 and C-3.

Figure 4A:
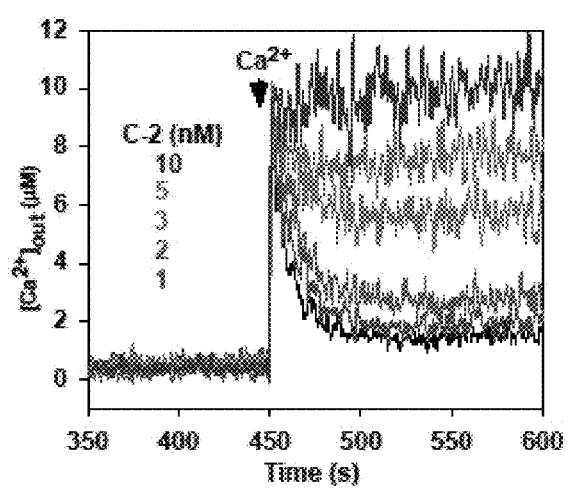
FIG. 4A includes representative traces of $[Ca^{2+}]_{out}$ clearance in permeabilized HEK293T cells challenged with a range of C-2 concentrations (1, 2, 3, 5, and 10 nM).
Figure 4B:
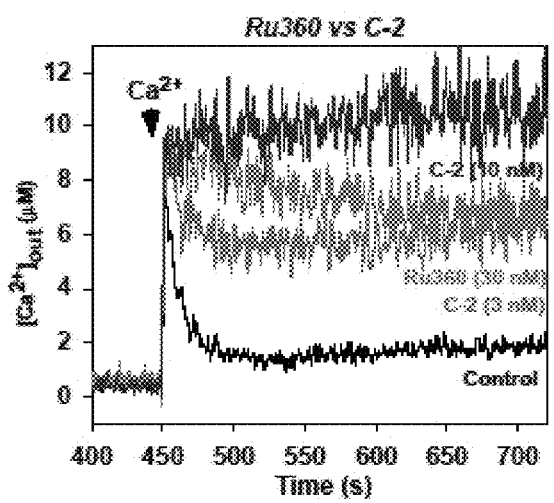
FIG. 4B is a graph comparing MCU-inhibitory effect by Ru360 (30 nM) and C-2 (2 and 10 nM) at lower concentrations.
Figure 4C:
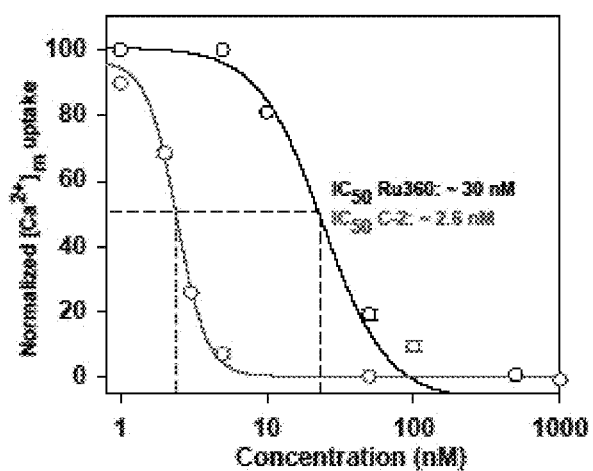
FIG. 4C is a graph showing calculation of dose-dependent $IC_{50}$ inhibition by C-2 and Ru360. Data represent mean±SEM (n=3-6).

Having identified (C-2 as a cell-permeable MCU inhibitor, a dose-response analysis was performed to determine the potency of C-2 towards $_mCa^{2+}$ uptake inhibition of C-2 in a permeabilized cell system. Permeabilized IHEK293T cells were treated with C-2 (1 nM to 1 μM). A 20 μM $Ca^{2+}$ bolus was added after baseline recording, and the extra-mitochondrial calcium cleared was used as an indicator for MCU-mediated $_mCa^{2+}$ uptake using Fura-2FF. The results are shown in FIGS. 4A-4C. FIG. 4A includes representative traces of $[Ca^{2+}]_{out}$ clearance in permeabilized HEK293T cells challenged with a range of C-2 concentrations (1, 2, 3, 5, and 10 nM). FIG. 4B is a graph comparing MCU-inhibitory effect by Ru360 (30 nM) and C-2 (2 and 10 nM) at lower concentrations. FIG. 4C is a graph showing calculation of dose-dependent $IC_{50}$ inhibition by C-2 and Ru360. Data represent mean±SEM (n=3-6), n.s.=not significant. The 50% maximal inhibitory concentration ($IC_{50}$) for $Ca^{2+}$ uptake in permeabilized cells was found to be 2.6 nM for C-2, which is an order of magnitude more effective than commercially available Ru360 ($IC_{50}$=30 nM) (FIG. 4C). Furthermore, complete inhibition of $_mCa^{2+}$ uptake was observed when cells were dosed with 10 nM C-2 while 500 nM of Ru360 was required for the same response (FIGS. 4A and 4B).

Figure 4D:
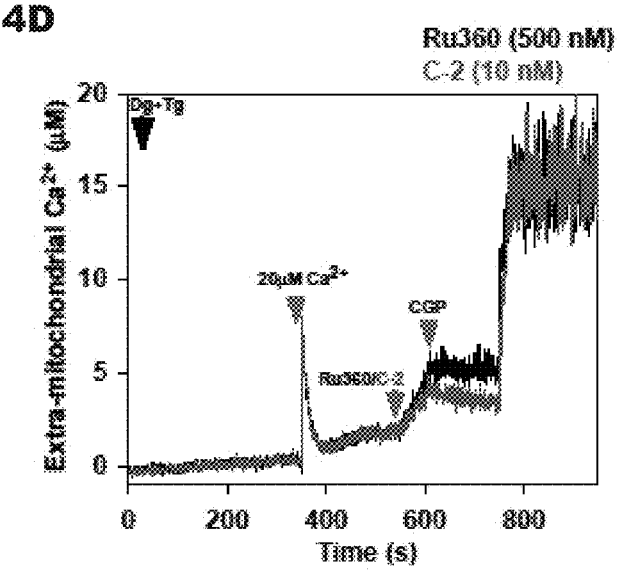
FIG. 4D is a graph showing assessment of mitochondrial $Ca^{2+}$ influx and efflux rates. Permeabilized HEK293T cells were pulsed with 20 μM $Ca^{2+}$ at 350 s to measure mitochondrial $Ca^{2+}$, uptake, followed by the addition of the 1 μM C-2 or Ru360 at 550 s, 10 μM CGP37157 at 600 s, and 6 μM CCCP at 750 s.
Figure 4E:
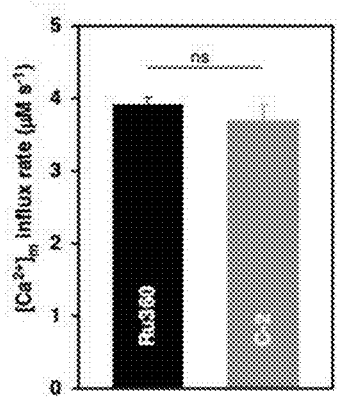
FIG. 4E is a bar chart showing quantification of $Ca^{2+}$ influx rate.
Figure 4F:
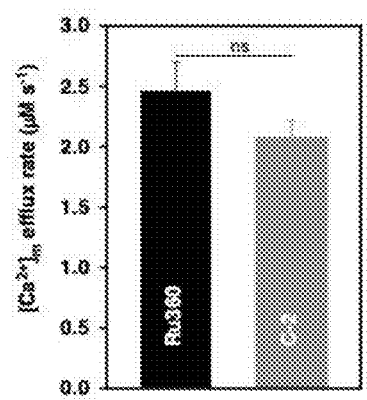
FIG. 4F is a bar chart showing quantification of $Ca^{2+}$ efflux rate after addition of C-2 or Ru360.
Figure 4G:
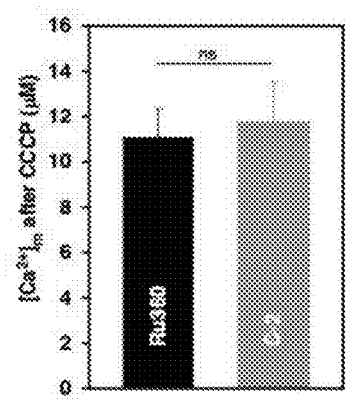
FIG. 4G is a bar chart showing quantification of CCCP-induced release of accumulated mitochondrial $Ca^{2+}$. (A, B). Data represent mean±SEM; **p<0.01; n=4.

FIG. 4D is a graph showing assessment of mitochondrial $Ca^{2+}$ influx and efflux rates. Permeabilized HEK293T cells were pulsed with 20 μM $Ca^{2+}$ at 350 s to measure mitochondrial $Ca^{2+}$ uptake, followed by the addition of the 1 μM C-2 or Ru360 at 550 s, 10 μM CGP37157 at 600 s, and 6 μM CCCP at 750 s. In FIG. 4D, a representative trace depicts the comparison of C-2 and Ru360. FIG. 4E is a bar chart showing quantitation of $Ca^{2+}$ influx rate. FIG. 4F is a bar chart showing quantification of $Ca^{2+}$ efflux rate after addition of C-2 or Ru360. FIG. 4G is a bar chart showing quantification of CCCP-induced release of accumulated mitochondrial $Ca^{2+}$. For C-2 to be an effective $_mCa^{2+}$ uptake inhibitor, C-2 should selectively inhibit MCU-mediated $Ca^{2+}$ uptake and not interact with other cellular ion channels. Despite showing greatly reduced $_mCa^{2+}$ uptake, intact cells treated with C-2 showed normal cytosolic calcium dynamics when stimulated with histamine (FIGS. 4D and 4F). To further confirm the selectivity of C-2 for the MCU, $_mCa^{2+}$ uptake, $_mCa^{2+}$ efflux rates and matrix $Ca^{2+}$ levels were measured in permeabilized HEK293T cells before and after treatment with C-2 using the fluorescent $Ca^{2+}$ indicator Fura-2-FF. Untreated cells displayed normal $[Ca^{2+}]_o$ clearance rates (FIG. 4D)). Ru360 or C-2 were next added to inhibit MCU-mediated $Ca^{2+}$ uptake and subsequently visualize $[Ca^{2+}]_m$ efflux (FIG. 4D). $[Ca^{2+}]_m$ efflux rates were similar between both inhibitors, which suggests that Ru360 and C-2 selectively inhibit the MCU and do not affect $_mCa^{2+}$ efflux channels (FIGS. 4E-4G). To further confirm that C-2 did not affect mitochondrial calcium efflux, cells were treated with the sodium calcium exchanger (NCLX) inhibitor CGP-37157 (M. Chiesi et al., Biochem. Pharmacol. 1988, 37, 4399-4403). No change was observed in C-2 activity upon treatment with CGP-37157 and CCCP (FIGS. 4E, 4F, and 4G). These results indicate that Ru360 and C-2 do not interact with other mitochondrial calcium transport proteins and selectively interact with the MCU.

Exploring the Mechanism of MCU Inhibition

Figures 5A, 5B:
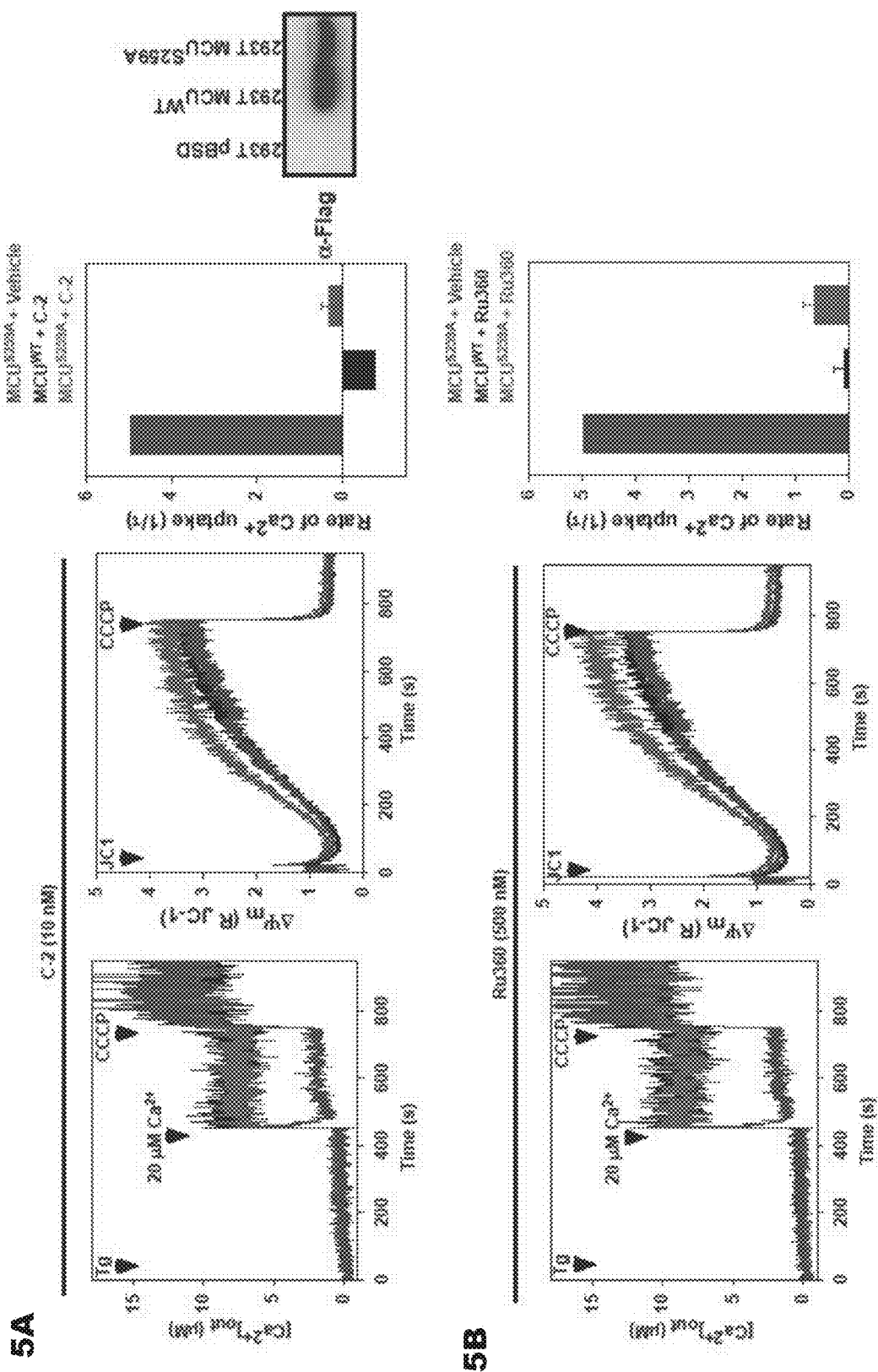
FIGS. 5A and 5B are representative traces of $[Ca^{2+}]_{out}$ clearance and $\Delta\Psi_m$. Permeabilized HEK293T cells stably expressing Flag tagged $MCU^{WT}$ and $MCU^{S259A}$ mutant challenged with either C-2 (10 nM) (FIG. 5A) or Ru360 (500 nM) (FIG. 5B). Bar graphs represent the quantification of the rate of $[Ca^{2+}]_m$ uptake.

Having observed the high potency of C-2 compared to Ru360, the mechanism of action of C-2 was next investigated. Site-directed mutagenesis revealed that the serine residue S259 of the human MCU is required for maximum activity of Ru360. Mutating this serine residue to an alanine (S259A) renders partial resistance to Ru360-mediated MCU inhibition (J. M. Baughman et al., Nature 2011, 476, 341-345). First, an experiment was undertaken to determine if interaction with the S259 residue on the MCU is necessary for C-2 to be effective. HIEK293T cells stably expressing flag-tagged full-length human wild type MCU ($MCU^{WT}$) or the mutant S259A ($MCU^{S259A}$) were permeabilized and $_mCa^{2+}$ uptake was measured as above. As shown by the results in FIG. 5A, cells expressing the $MCU^{S259A}$ mutation displayed partial resistance to Ru360 inhibition of the MCU compared to $MCU^{WT}$ cells. In contrast, as shown by the results in FIG. 5B, cells expressing the $MCU^{259A}$ mutation showed almost no change in the inhibitory activity of C-2 compared to the $MCU^{WT}$ cells. These results suggest that C-2 could inhibit the MCU in a manner distinct from Ru360.

Figures 5C, 5D:
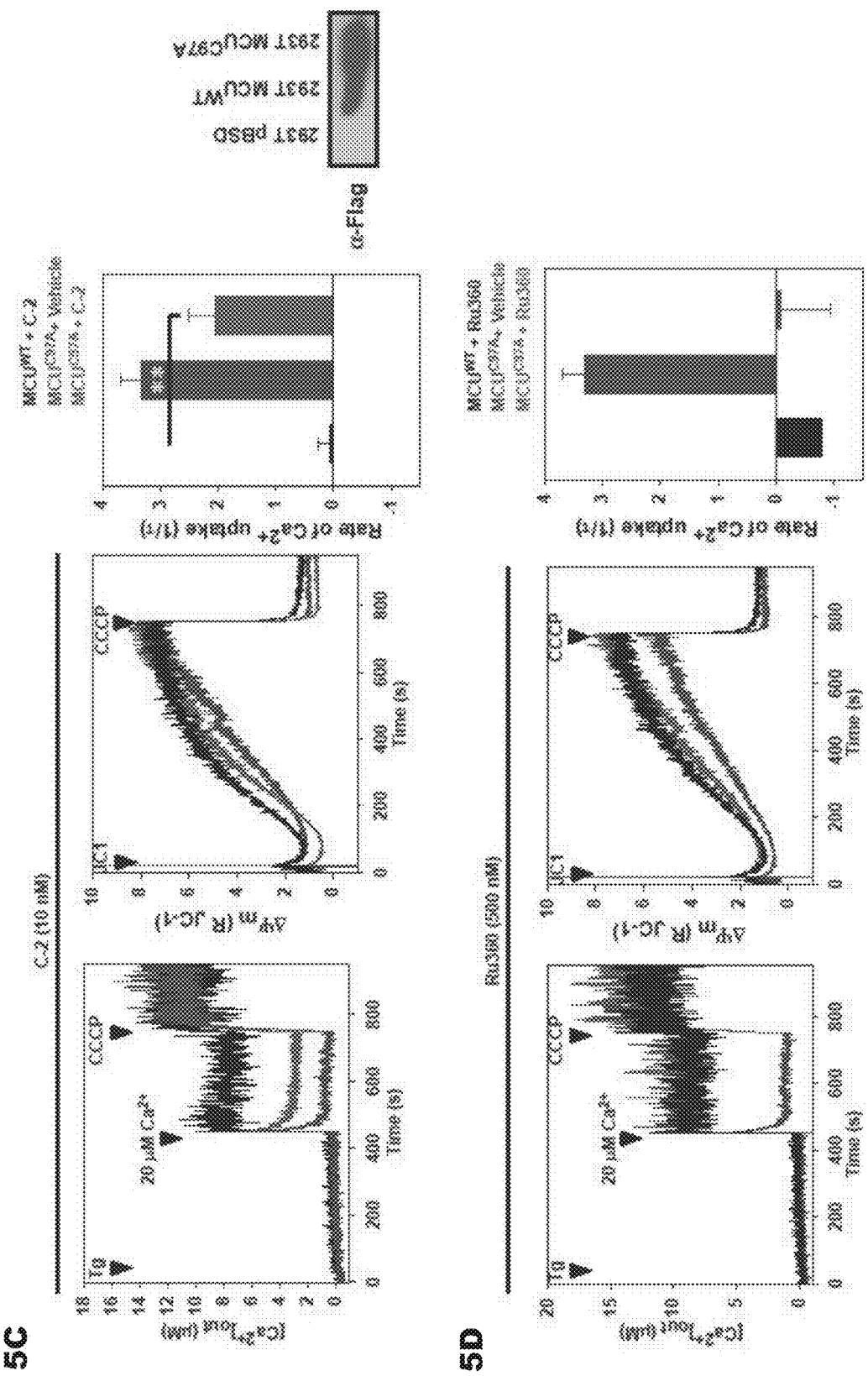
FIGS. 5C and 5D are representative traces of $[Ca^{2+}]_{out}$ clearance and $\Delta\Psi_m$ of HEK293T cells stably expressing Flag tagged $MCU^{WT}$ and $MCU^{C97A}$ mutant challenged with either C-2 (10 nM) (FIG. 5C) or Ru360 (500 nM) (FIG. 5D). Bar graphs represent the quantification of the rate of $[Ca^{2+}]_m$ uptake. The compound MCU inhibitory effect was compared with cells reconstituted with appropriate mutants alone. Data represent mean±SEM; **p<0.01; n=4. The far left panels in each of FIGS. 5A-5D show the cytosolic calcium levels as a function of time. Upon addition of $Ca^{2+}$, cells will gradually take up these ions in their mitochondria unless an inhibitor is present. The middle left panels in each of FIGS. 5A-5D) show the mitochondrial membrane potential as a function of time. The mitochondrial membrane potential remains intact in the presence of Ru265. The middle right panels in each of FIGS. 5A-5D show a bar graph representation of the data shown in the far left panels. Specifically, the rate of mitochondrial calcium uptake as measured from the calcium versus time plots is given for the cells under different conditions. The far right panels in FIGS. 5A and 5C show a Western blot, confirming the correct expression of the mutant MCU form.

It has recently been revealed that the conserved human MCU cysteine 97 residue located in the MCU-NTD (residues 72-189) in the mitochondrial matrix senses mitochondrial levels of reactive oxygen species and induces higher order oligomerization to regulate MCU channel activity (Dong et al., Mol. Cell 2017, 65, 1014-1028). Additionally, recent structural and biochemical studies, such as the foregoing, have demonstrated the importance of the NTD in MCU oligomerization and activity. To determine if C-2 interacts with the NTD, HEK293T cells stably expressing Flag-tagged full-length wild-type MCU ($MCU^{WT}$) and the mutant C97A ($MCU^{C97A}$) were permeabilized, and $_mCa^{2+}$ uptake was measured as above. Upon $MCU^{C97A}$ mutation, cells treated with C-2 showed significantly reduced MCU inhibitory activity compared to $MCU^{WT}$ cells, as shown in FIG. 5C. In contrast, the $MCU^{C97A}$ mutation had almost no effect on the activity of Ru360, as shown in FIG. 5D. Taken together, these studies suggest that C-2 and Ru360 may act on different regions of the MCU to inhibit mitochondrial calcium uptake.

To further elucidate the potential interaction of C-2 with the MCU-NTD, the interaction between C-2 and the uniformly $^{15}$N-labeled recombinant human MCU-NTD (residues 72-189) was investigated using solution nuclear magnetic resonance (NMR) spectroscopy. The $^1$H-$^{15}$N-heteronuclear single quantum coherence (HSQC) spectrum of the MCU-NTD in the absence of C-2 showed well-dispersed amide H(N) crosspeaks with homogeneous peak intensities, consistent with the well-folded and soluble domain. Remarkably, upon addition of a 3-fold molar excess of C-2, the NMR sample showed a rapid formation of insoluble precipitate. A similar addition of C-2 to sample buffer alone showed neither precipitate formation nor a change in pH, suggesting that the insoluble aggregate contained MCU-NTD. Consistent with precipitation of the protein, the $^1$H-$^{15}$N-HSQC spectrum of the 1:3 MCU-NTD:C-2 sample mixture showed a drastic loss in most H(N) crosspeak intensities. It is noteworthy that some of the remaining H(N) peaks of the protein also exhibited small chemical shift perturbations.

To determine if the MCU-NTD remained intact upon treatment with C-2, the insoluble aggregate (Insol.+C-2) was resuspended in loading dye and the migration of the protein was compared to untreated soluble MCU-NTD (Sol.) by SDIS-PAGE analysis. After Coomassie blue staining, the untreated MCU-NTD control showed clear bands, which indicated the presence of the monomer (~13.9 kDa) in addition to low levels of the dimer and tetramer oligomers, which is characteristic of the native MCU-NTD conformation. The protein precipitate that formed upon treatment with C-2 showed a distinct and systematic laddering corresponding to the presence of monomer, dimer, trimer, tetramer, and higher aggregate formation. The appearance of the trimer and higher order aggregates upon treatment with C-2 may indicate that the MCU-NTD conformation induced by C-2 is different from that of the native conformation. Similar MCU-NTD aggregation was observed when the MCU-NTD was treated with lower molar ratios (i.e. 1:2 and 1:1) of C-2.

To distinguish whether C-2 induced a global or more local structural effect on the MCU-NTD, peaks exhibiting an intensity reduction of a ≥40% were mapped. Remarkably, the most severely affected H—(N) crosspeaks were found to cluster close together on the two β-sheets of the 3-grasp-like fold, despite the long distance between these residues in sequence space. The clustering of these perturbations could be a result of i) direct binding with the compound, ii) indirect effects of the lower soluble protein concentration shifting the self-association equilibrium, or iii) C-2-mediated modifications to the protein. Nevertheless, these data collectively suggest that C-2 interacts with the MCU-NTD) to induce aggregation of the protein and inhibit $Ca^{2+}$ uptake through the MCU channel. Notably, it has herein been found that commercially available Ru360 also interacts with the purified MCU-NTD in a cell-free system, giving rise to precipitation and systematic laddering. However, site-mutagenesis studies with $MCU^{C97A}$ and $MCU^{S259A}$ (FIGS. 5A-5D) clearly show that the inhibitory activity of C-2 is dependent on the mutation-status of the NTD, whereas the inhibitory activity of Ru360 is not. Thus, the NTD may be a potent target for MCU inhibition that is only accessible to C-2 because of its enhanced membrane permeability when compared to Ru360.

Protection from $Ca^{2+}$-Induced PTP Opening and Hypoxia/Reoxygenation Injury

Given the $Ca^{2+}$ uptake inhibiting properties and low toxicity of C-2, C-2 was studied for its possible ability to protect cardiomyocytes from the $_mCa^{2+}$ overload that occurs during hypoxia/reoxygenation (I-H/R) injury and prevent mPTP opening and mitochondrial swelling. Freshly isolated neonatal rat ventricular myocytes (NRVMs) treated with C-2 (50 μM) were subjected to 16 hours of hypoxia (1% $O_2$-5% $CO_2$), followed by 8 hours of reoxygenation (21% $O_2$-5% $CO_2$). Untreated NRVMs served as controls. After H/R injury, NRVMs were permeabilized and loaded with the JC-1 and Fura-FF to simultaneously measure $\Delta\Psi_m$ and $_mCa^{2+}$ uptake.

Cells treated with C-2 maintained mitochondrial integrity with no loss of $\Delta\Psi_m$ after H/R-injury. Additionally, treatment with C-2 resulted in complete ablation of $_mCa^{2+}$ uptake after H/R injury. On the contrary, untreated cells subjected to identical conditions showed no preservation of $\Delta\Psi_m$ and did not show normal $_mCa^{2+}$ uptake. In contrast to C-2, pretreatment with Ru360 did not prevent H/R-mediated $\Delta\Psi_m$ dissipation. Additionally, the swelling of mitochondria isolated from NRVMs subjected to H/R injury in the absence or presence of C-2 or Ru360 was monitored. After baseline measurement of the absorbance at 600 nm, a single bolus of $Ca^{2+}$ (250 μM) was added to induce mPTP opening. As known, the decrease in mitochondrial absorbance indicates mitochondrial swelling and subsequent mPTP opening. When cells were treated with C-2 or Ru360, no decrease in absorbance was observed after $Ca^{2+}$ addition, which indicates lack of mitochondrial swelling. These results demonstrate that inhibition of MCU-mediated $_mCa^{2+}$ uptake by C-2 effectively prevents mPTP opening in response to H/R and when challenged with high $Ca^{2+}$ concentrations.

Given the importance of $_mCa^{2+}$ in mitochondrial bioenergetics, damage, and cell death, identification of effective MCU-mediated $_nCa^{2+}$ uptake inhibitors have attracted considerable interest. In this report, the synthesis, characterization, and biological activity of a cell-permeable, highly potent and selective MCU inhibitor has been described. Identifying potent and selective MCU inhibitors has proven to be challenging, with reported potential inhibitors generally exhibiting low permeability or poor selectivity and mitochondrial targeting (D. M. Arduino et al., *Mol. Cell* 2017, 67, 711-723.e7). The syntheses of the oxo-bridged complexes Ru360 and C-1 are low-yielding and require tedious chromatographic purification (S. R. Nathan et al., *Inorg. Chem.* 2017, 56, 3123-3126 and S. R. Nathan et al., *J. Vis. Exp.* 2017, 56527), In contrast, C-2 (herein also referred to as Ru265) and C-3 can be prepared in moderate yields without the need for extensive purification. Additionally, the nitrido-bridged complexes can be accessed through a common starting material, $K_3[Ru_2(μ-N)Cl_8(OH_2)_2]$. This synthetic route permits the facile design of related analogues of Ru265 and C-3 through ligand substitution reactions. This straightforward chemical reaction is advantageous for studying structure-activity relationships to probe the biological activity of these complexes.

Among the compounds studied, Ru265 (C-2) showed the most effective MCU-inhibition in non-permeabilized cells. Furthermore, this compound is highly water soluble (1 mg/mL) and exhibits low toxicity to human cells. The low toxicity of these complexes is significant because of the large number of known cytotoxic ruthenium compounds (e.g., E. Alessio, *Eur. J. Inorg Chem.* 2017, 1549-1560. The minimal toxicity of Ru265 in contrast to many other ruthenium compounds highlights the importance of molecular structure and coordination geometry in the biological activity of metal-based compounds. In the intact cellular models, Ru265 consistently inhibited MCU-mediated $_mCa^{2+}$ uptake without any effect on intracellular $Ca^{2+}$ dynamics.

A series of recent reports have definitively elucidated the structure of the full-length MCU through cryo-EM and X-ray crystallographic techniques (e.g., R. Baradaran et al., *Nature* 2018, 559, 580-584). Most notably, these reports highlight the assembly of the NTD directly under the channel pore in the mitochondrial matrix. The binding studies conducted herein suggest that Ru265 interacts with the MCU-NTD and may perturb the assembly of NTD through aggregation, thereby inhibiting normal channel function. Based on these data, it may be deduced that the Ru265-dependent aggregation of NTD) could inhibit the dynamics of the NTD and immediately adjacent coiled-coiled domains required to regulate pore opening and closing. This hypothesis is supported by the lack of rapid MCU $Ca^{2+}$ uptake inhibition at lower Ru265 concentrations (FIGS. 4A-4C). It remains to be definitively determined whether Ru265-induced NTD aggregation regulates the $Ca^{2+}$ binding and release mechanism. Alternatively, binding of Ru265 to the NTD could modulate MCU channel activity by promoting conformations which constrict the pore.

It has previously been shown that human MCU-NTD contains a contiguous electronegative surface patch that can bind divalent cations and inhibit the MCU channel function via a shift of the self-association equilibrium of the domain toward monomer formation (S. K. Lee et al., *Cell Chem. Biol.* 2016, 23, 1157-1169). Given the charge, symmetry, and size of Ru265, it is possible that Ru265 also interacts with the MRAP of the MCU-NTD, with the ability to bridge MCU-NTD subunits. Using Ru265, a robust inhibition of the MCU channel was observed, which may be a consequence of the higher order oligomerization of the MCU-NTD that it induces. In the context of the fill-length MCU, the bridging of dimers could prevent MCU-NTD dimer dynamics proposed to be involved in MCU gating by locking the domains in an assembly pattern, thereby promoting a closed pore and inhibited $Ca^{2+}$ uptake.

In summary, the above experiments demonstrate a ruthenium-based complex that not only inhibits MCU selectively in vitro but also efficiently inhibits MCU activity and prevents loss of mitochondrial membrane potential dissipation, mitochondrial swelling, and mPTP opening in cells exposed to simulated ischemic reperfusion injury. The above experiments show that Ru265 is over 10 times more effective at inhibiting $_mCa^{2+}$ uptake than Ru360, and potentially interacts with the matrix side of the MCU rather than the intermembrane $Ca^{2+}$ binding sites. Moreover, Ru265 inhibits MCU activity without disrupting normal cellular $Ca^{2+}$ dynamics.

While there have been shown and described what are at present considered the preferred embodiments of the invention, those skilled in the art may make various changes and modifications which remain within the scope of the invention defined by the appended claims.

What is claimed is:

1. A method for treating or preventing reperfusion injury, the method comprising administering to a subject having or at risk for said reperfusion injury a therapeutically effective amount of an inhibitor of the mitochondrial calcium uniporter, wherein said inhibitor is a compound having the following structure:

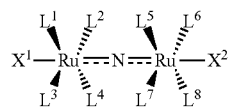
(1)

wherein:
$L^1$, $L^2$, $L^3$, $L^4$, $L^5$, $L^6$, $L^7$, and $L^8$ are —$NH_3$ groups, wherein optionally, one or more pairs of adjacent —$NH_3$ groups interconnect with a —$CH_2CH_2$— linkage to form a bidentate ethylenediamine group of the formula —$H_2N$—$CH_2CH_2$—$NH_2$;
$X_1$ and $X_2$ are selected from halide atoms;
and wherein the inhibitor compound shown in Formula (1) has an overall positive charge dependent on the oxidation state of the Ru atoms.

2. The method of claim 1, wherein said reperfusion injury is in cardiac tissue.

3. The method of claim 1, wherein said reperfusion injury is in brain tissue.

4. The method of claim 3, wherein said reperfusion injury in brain tissue is associated with a stroke.

5. The method of claim 1, wherein said reperfusion injury is associated with organ transplantation.

6. The method of claim 1, wherein said method treats reperfusion injury by resulting in at least partial restoration of bodily tissue that has been damaged by an ischemic event followed by reperfusion injury.

7. The method of claim 1, wherein at least two adjacent —$NH_3$ groups are interconnected.

8. The method of claim 1, wherein the —$NH_3$ groups are not interconnected.

9. The method of claim 1, wherein the inhibitor is selected from the following structures:

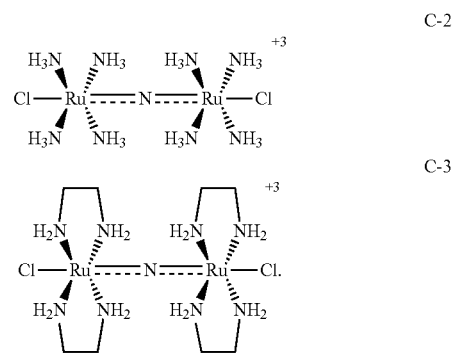

10. A method of inhibiting mitochondrial calcium uniporter, the method comprising contacting a cell with an inhibitor having the following structure:

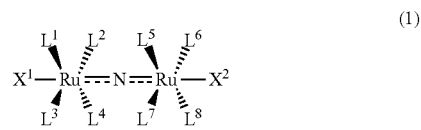
(1)

wherein:
$L^1$, $L^2$, $L^3$, $L^4$, $L^5$, $L^6$, $L^7$, and $L^8$ are —$NH_3$ groups, wherein optionally, one or more pairs of adjacent —$NH_3$ groups interconnect with a —$CH_2CH_2$— linkage to form a bidentate ethylenediamine group of the formula —$H_2N$—$CH_2CH_2$—$NH_2$;
$X_1$ and $X_2$ are selected from halide atoms; and
wherein the inhibitor compound shown in Formula (1) has an overall positive charge dependent on the oxidation state of the Ru atoms.

11. The method of claim 10, wherein at least two adjacent —$NH_3$ groups are interconnected.

12. The method of claim 10, wherein the —$NH_3$ groups are not interconnected.

13. The method of claim 10, wherein the inhibitor is selected from the following structures:

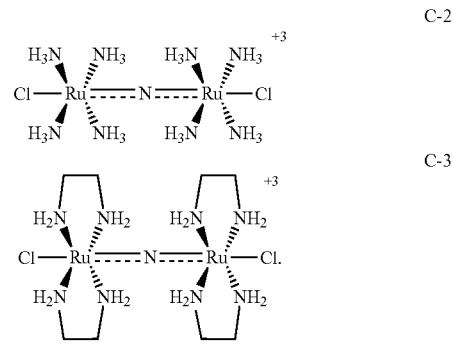

* * * * *